United States Patent [19]
Lee et al.

[11] Patent Number: 5,183,906
[45] Date of Patent: Feb. 2, 1993

[54] 2- AND 5-ALKYL AND PHENYL SUBSTITUTED 4-(1-HYDROXY, 1-ACYLOXY OR 1-CARBAMOYLOXY)-5-HYDROXY-2 (5H)-FURANONES AS ANTI-INFLAMMATORY AGENTS

[75] Inventors: Gary C. M. Lee, Laguna Hills; Michael E. Garst, Newport Beach; George Sachs, Encino, all of Calif.

[73] Assignee: Allergan, Inc., Irvine, Calif.

[21] Appl. No.: 693,204

[22] Filed: Apr. 30, 1991

[51] Int. Cl.$^5$ .................. C07F 9/09; C07D 307/34
[52] U.S. Cl. ................................ 549/218; 549/313; 549/318
[58] Field of Search ................ 549/218, 313, 318

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. |
| 209274 | 1/1987 | European Pat. Off. |
| 295056 | 6/1987 | European Pat. Off. |
| 350878 | 1/1990 | European Pat. Off. |

OTHER PUBLICATIONS

Bonjuklian, et al., Chemical Abstracts, vol. 106, 156260c, p. 670 (1987).
Reynolds, et al., J. Am. Chem. Soc., 110, pp. 5172-5177 (1988).
Tocanne, et al., Chemical Abstracts 69 76581k, p. 7146 (1968).
Deems, et al., Biochimica et Biophysica Acta, 917 pp. 258-268 (1987).
Scheuer, et al., Journal of the American Chemical Society 100:1 p. 307 (Jan. 4, 1978).
Graziano, et al., Chemical Abstracts 107, (1987), 236559t.
Roll, et al., Org. Chem. 1988, 53 3276-8.
Negishi et al., J. Org. Chem 45, pp. 5223-5225, (1980).
E. D. de Silva et al., "Tetrahedron Letters", 21:1611-1614 (1980).
Nakagawa et al., "Aldose reductase inhibitor from Palaun Sponges" Chem. Abstract 106: 96126b.
Tanaka, et al., The Chemical Society of Japan, Chemistry Letters, pp. 633-636 (1983).
Tanis, et al., Tetrahedron Letters, vol. 25, No. 40, pp. 4451-4454 (1984)—Furans in Synthesis 4. Silyl Furans as Butenolide Equivalents.
Graziano, et al., "Photosensitized Oxidation of Furans, Part 12, Solvent Effects in Thermal Rearrangement of the 2,5-Peroxides of 2,5-Unsubstituted Furans", CA 107 (25) 236559t.
David, Nettleton et al., Inflammation Research Association, Fifth International Conference Poster Session, Phospholipase A$_2$ Inhibition by Dihydrofuranones, Sep. 23-27, 1990.

Primary Examiner—C. Warren Ivy
Assistant Examiner—Amelia A. Owens
Attorney, Agent, or Firm—Gabor L. Szekeres; Martin A. Voet; Robert J. Baran

[57] ABSTRACT

Novel anti-inflammatory furanone compounds have the following formula

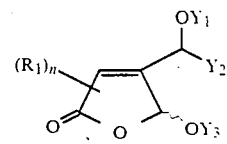

where $R_1$ independently is H, phenyl, $C_1-C_6$ alkyl substituted phenyl, halogen substituted phenyl, or alkyl of 1 to 6 carbons and n is an integer having the values of 1 or 2, and where when n is 1 the $R_1$ group is attached either to the 3 or to the 5 position of the 2-furanone, when n is 2 then $R_1$ is attached to both the 3 and 5 positions, with the proviso that when n is 1 then $R_1$ is not H; $Y_1$ is H, alkyl of 1 to 20 carbons, phenyl $C_1-C_{20}$ alkyl, $C_1-C_{20}$ alkenyl containing one or more olephinic bonds, $PO(OH)_2$, $PO(OH)OR_2$, $PO(OH)R_2$, $PO(OR_2)_2$, where $R_2$ is independently alkyl of 1 to 20 carbons, phenyl, or halogen substituted phenyl or $C_1-C_6$ alkyl substituted phenyl, further $Y_1$ is $CO-R_3$, $CO-OR_3$, $CONHR_3$, $SO_2R_3$, $SO_2NHR_3$, $(CH_2)_p-O-R_3$, or $(CH_2)_p-O-(CH_2)_m-O-R_3$, where p, and m, are integers and are independently 1 to 20 and $R_3$ is H, $C_1-C_{20}$ alkyl, $C_1-C_{20}$ alkenyl containing one or more olephinic bonds, phenyl, halogen substituted phenyl or $C_1-C_6$ alkyl substituted phenyl, with the proviso that when $Y_1$ is $CO-R_3$, $CO-OR_3$, and $CONHR_3$ then $R_3$ is not hydrogen; $Y_2$ is H, an alkyl group of 1 to 25 carbons, phenyl, naphthyl, phenyl ($C_1-C_{20}$)alkyl-, naphthyl ($C_1-C_{20}$)alkyl-, halogen substituted phenyl, $C_1-C_6$ alkyl substituted phenyl, halogen substituted naphthyl, $C_1-C_6$ substituted naphthyl; $Y_3$ is H, alkyl of 1 to 20 carbons, $CO-R_4$, $CO-O-R_4$, $CO-NH-R_4$, $PO-(OR_4)_2$ or $PO(OR_4)R_4$, where $R_4$ independently is H, alkyl of 1 to 20 carbons, phenyl, or halogen substituted phenyl or $C_1-C_6$ alkyl substituted phenyl.

28 Claims, No Drawings

2- AND 5-ALKYL AND PHENYL SUBSTITUTED 4-(1-HYDROXY, 1-ACYLOXY OR 1-CARBAMOYLOXY)-5-HYDROXY-2 (5H)-FURANONES AS ANTI-INFLAMMATORY AGENTS

FIELD OF THE INVENTION

The present invention is directed to novel 2- and 5-alkyl phenyl substituted 4-(1-hydroxy-, 1-acyloxy-, or 1-carbamoyloxy) 5-hydroxy-2(5H)-furanones which compounds are active as anti-inflammatory agents. The present invention is also directed to pharmaceutical compositions which comprise one or more of the novel compounds of the invention, to the methods of using these pharmaceutical compositions, and to the chemical processes of making the novel compounds.

BRIEF DESCRIPTION OF THE PRIOR ART

Manoalide is a compound isolated from a marine sponge [E. D. de Silva et al., Tetrahedron Letters 21:1611-1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manoalide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

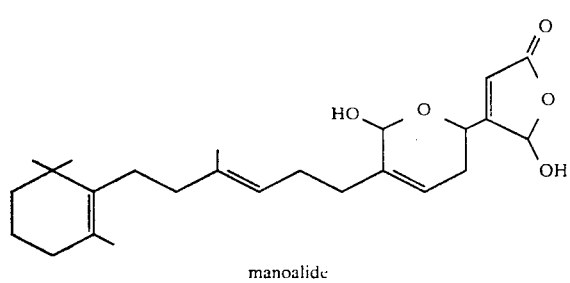

manoalide

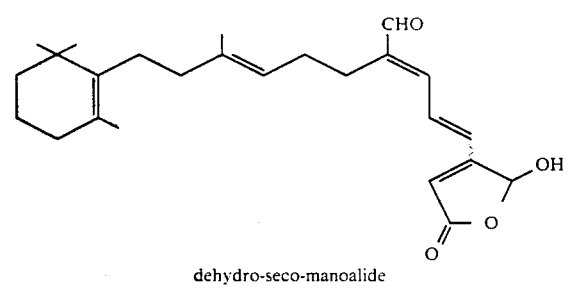

dehydro-seco-manoalide

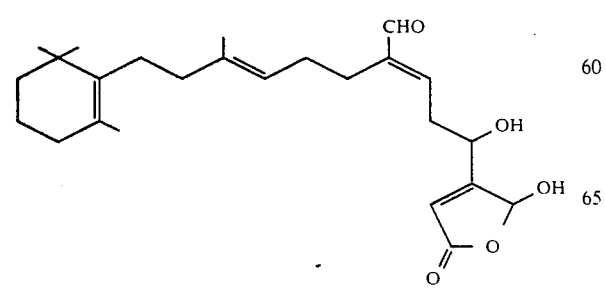

seco-manoalide

Synthetic analogs of manoalide, particularly analogs various substituents on the furanone moiety of manoalide, are described in several applications for U.S. Letters Patent by the same inventor as in the present application, the following of which have been allowed and are expected to issue as U.S. Letters Patent:

Ser. No. 281,126 filed on Dec. 7, 1988.

Published European Patent Application No. 0 295 056 discloses 4-substituted 5-hydroxy-2(5H)-furanones having anti-inflammatory immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

2-Substituted 4-furaldehydes (5-substituted 3-furaldehydes) are described in U.S. Pat. No. 4,935,530.

SUMMARY OF THE INVENTION

The present invention covers compounds of Formula 1

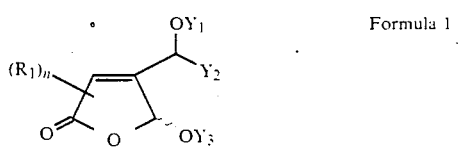

Formula 1 where
$R_1$ independently is H, phenyl, $C_1$-$C_6$ alkyl substituted phenyl, halogen substituted phenyl, or alkyl of 1 to 9 carbons and n is an integer having the values of 1 or 2, and where when n is 1 the $R_1$ group is attached either to the 3 or to the 5 position of the 2-furanone, when n is 2 then $R_1$ is attached to both the 3 and 5 positions, with the proviso that when n is 1 then $R_1$ is not H;

$Y_1$ is H, alkyl of 1 to 20 carbons, phenyl $C_1$-$C_{20}$ alkyl, $C_1$-$C_{20}$ alkenyl containing one or more olefinic bonds, $PO(OH)_2$, $PO(OH)OR_2$, $PO(OH)R_2$, $PO(OR_2)_2$, where $R_2$ is independently alkyl of 1 to 20 carbons, phenyl, halogen substituted phenyl or $C_1$-$C_6$ alkyl substituted phenyl, further $Y_1$ is $CO-R_3$, $CO-OR_3$, $CONHR_3$, $SO_2R_3$, $SO_2NHR_3$, $(CH_2)_p-O-(CH_2)_m-O-R_3$, where p, and m, are integers and are independently 1 to 20 and $R_3$ is H, $C_1$-$C_{20}$ alkyl, $C_1$-$C_{20}$ alkenyl containing one or more olefinic bonds, phenyl, halogen substituted phenyl or $C_1$-$C_6$ alkyl substituted phenyl, with the proviso that when $Y_1$ is $CO-OR_3$ or $CONHR_3$ then $R_3$ is not hydrogen;

$Y_2$ is H, an alkyl group of 1 to 25 carbons, phenyl, naphthyl, phenyl ($C_1$-$C_{20}$)alkyl-, naphthyl ($C_1$-$C_{20}$)alkyl-, halogen substituted phenyl, $C_1$-$C_6$ alkyl substituted phenyl, halogen substituted naphthyl, $C_1$-$C_6$ substituted naphthyl; $Y_3$ is H, alkyl of 1 to 20 carbons, $CO-R_4$, $CO-O-R_4$, $CO-NH-R_4$, $PO(OR_4)_2$ or $PO(OR_4)R_4$, where $R_4$ independently is H, alkyl of 1 to 20 carbons, phenyl, or halogen substituted phenyl or $C_1$-$C_6$ alkyl substituted phenyl, with the provisio that when $Y_3$ is $COOR_4$ or $CONHR_4$ then $R_4$ is not H.

The present invention also covers salts of the above-defined compounds, formed with pharmaceutically acceptable acids or bases, as applicable.

In a second aspect the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

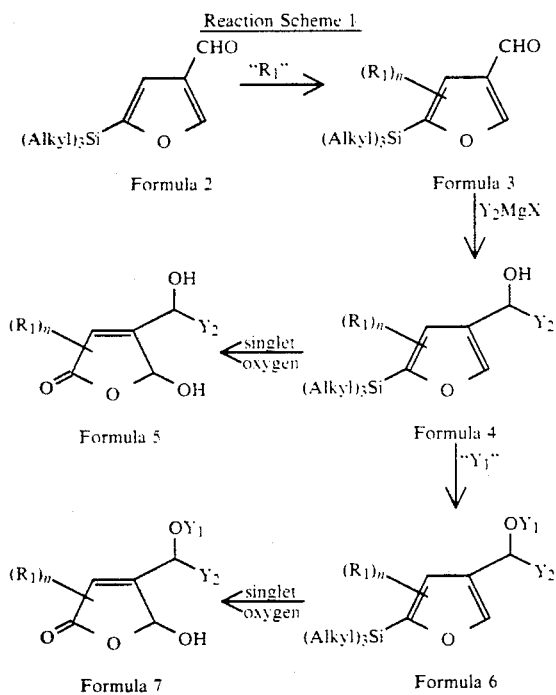

In still another aspect, the present invention relates to the processes of making the compounds of Formula 1. In general terms, these processes, shown in a summarized fashion in Reaction Scheme 1 comprises the steps of introducing the $R_1$ group (or groups) into the 3 or 5 position, or both, of a 2-trialkylsilyl-4-furaldehyde (Formula 2), such as 2-trimethylsilyl-4-furaldehyde or 2-triethylsilyl-4-furaldehyde. Thereafter, the resulting 3- or 5- substituted, or 3,5-disubstituted 2-trialkylsilyl-4-furaldohyde (Formula 3) is reacted with a Grignard (or like) reagent of the general formula $Y_2$—Mg—X (where X is halogen) to provide a 4-(alpha-hydroxy) substituted 3- or 5-substituted, or 3,5-disubstituted -2-trialkylsilyl-4-furan of Formula 4. The compounds of Formula 4 may be subjected to oxydation with singlet oxygen to provide 3- or 5- substituted, or 3,5-disubstituted 5-hydroxy 4-(alpha-hydroxy) substituted 2-furanone compounds of Formula 5. Alternatively, the compounds of Formula 4 are alkylated, acylated, reacted with an isocyanate, with a substituted sulfonyl chloride, with a N-substituted sulfonamid chloride, substituted phosphonyl chloride etc., to introduce the $Y_1$ group as a substituent in the alpha hydroxy function in the side chain of the 4-position of the furan nucleus. The resulting compounds are shown by the general Formula 6. Compounds of Formula 6 are oxydized with singlet oxygen to provide compounds of Formula 7. The compounds of Formula 7 can be alkylated, acylated (or a $Y_3$ group other than alkyl or acyl can be introduced) in the 5-hydroxy moiety in conventional manner. In Formulas 2–7 the symbols $Y_1$, $Y_2$, $Y_3$, $R_1$ and n are defined as in connection with Formula 1.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Certain compounds of the invention contain a chiral center at the alpha carbon in the side chain on the 4-position of the 2(5H)-furanone moiety. Other compounds of the invention may contain more than one chiral center. Accordingly, the compounds of the invention may be prepared as mixtures of enantiomeric compounds (where the enantiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diasteromeric compound may be sterically and optically pure. However, all of the above-noted forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention, with reference to Formula 1 and with respect to the $R_1$ substituent are those where $R_1$ is alkyl of 1 to 6 carbons, more preferably methyl or butyl, and where $R_1$ is phenyl.

With respect to $Y_1$ in Formula 1 the compounds of the invention are preferred where $Y_1$ is H, acyl, more preferably acetyl, and where $Y_1$ represents a phenylcarbamoyl ($C_6H_5$—NH—CO—) group. $Y_1$ also preferably represents a lauroyl ($CH_3$—$(CH_2)_{10}$—CO) group, particularly when $Y_2$ is H.

With respect to $Y_2$ of Formula 1 compounds are preferred in accordance with the present invention where $Y_2$ is long chain normal alkyl, preferably normal alkyl of 8 to 25 carbon atoms; particularly preferred are compounds where $Y_2$ represents a normal dodecyl group.

The $Y_3$ group of Formula 1 is preferably H, or acetyl.

With respect to n, compounds are preferred where n is 1; also preferred are the compounds where n is 2 and where $Y_2$ is H.

The most preferred compounds of the invention are listed below with reference to Formula 8.

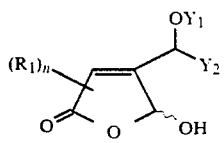

Formula 8

Compound 1: n=1, $R_1$=5-methyl, $Y_1$=$CH_3CO$; $Y_2$=$(CH_2)_{11}$—$CH_3$
Compound 2: n=1, $R_1$=3-methyl, $Y_1$=$CH_3CO$; $Y_2$=$(CH_2)_{11}$—$CH_3$
Compound 3: n=1, $R_1$=3-methyl, $Y_1$=$C_6H_5$—NHCO; $Y_2$=$(CH_2)_{11}$—$CH_3$
Compound 4: n=1, $R_1$=5-methyl, $Y_1$=$C_6H_5$—NHCO; $Y_2$=$(CH_2)_{11}$—$CH_3$
Compound 5: n=1, $R_1$=5-butyl, $Y_1$=$C_6H_5$—NHCO; $Y_2$=$(CH_2)_{11}$—$CH_3$
Compound 6: n=2, $R_1$=3-phenyl, $R_1$=methyl, $Y_1$=CO—$(CH_2)_{10}$—$CH_3$; $Y_2$=H
Compound 7: n=1, $R_1$=5-methyl, $Y_1$=CO—$(CH_2)_{10}$—$CH_3$; $Y_2$=H
Compound 8: n=1, $R_1$=3-phenyl, $Y_1$=$C_6H_5$—NHCO; $Y_2$=$(CH_2)_{11}$—$CH_1$
Compound 9: n=1, $R_1$=3-phenyl, $Y_1$=$CH_3CO$; $Y_2$=$(CH_2)_{11}$—$CH_3$ The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula 1, and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (Mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5-10 min trypsin-EDTA treatment whereas GH$_3$ cells were treated 2 to 5 min with a 1% pancreatin solution. Cells were immediately washed twice in a 20 mM HEPES buffer (pH 7.4) containing 120 mM NaCl, 6 mM KCl, 1 mM MgSO$_4$, 1 mg/ml glucose and 1 mg/ml pyruvate and 1.4 mM calcium (medium A). Approximately $5 \times 10^6$ cells were suspended in medium A and incubated with 4uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. [Ca$^{2+}$]i was calculated using the following formula:

$$[Ca^{2+}]_i = 220 \times \frac{F - F\min}{F\max - F}$$

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and Ca$^{2+}$chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900-904].

Inhibition of Phospholipase A$_2$

The effect of compounds of this invention on bee venom phospholipase A$_2$ is determined by the following procedure:

a. Bee venom phospholipase A$_2$ in 10 uM HEPES (pH 7.4) with 1 mM CaCl$_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-(1 — $^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5 M $H_2SO_4$ (40:10:1; v:v:v:).
f. 2 0 ml n-heptane and 1.0 ml $H_2O$ added; mixture centrifuged.
g. 2.0 ml n-heptane removed and treated with 200-300 mg of silica gel HR60.
h. Sample centrifuged; 1 ml of n-heptane SN removed and added to 10 ml scintillation fluid.
i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587-593 (1987).

ACTIVITY DATA

In the above-described phospholipase $A_2$ assay and Calcium$^{2+}$ channel mobilization assay the compounds of the invention were found to provide 50% inhibition ($IC_{50}$) at the following concentrations (in micromoles), as indicated in Table 1.

TABLE 1

| Phospholipase $A_2$ Assay. | |
|---|---|
| Compound name or number | $IC_{50}$ (micromolar) |
| 1 | 0.06 |
| 2 | >1 |
| 4 | 0.24 |
| manoalide | 0.03 |

| Calcium$^{2+}$ Channel Mobilization Inhibition Assay | | |
|---|---|---|
| | $IC_{50}$ (micromolar) | |
| Compound name or number | TRH induced | KCl induced |
| 1 | 2.5 | 7 |
| 4 | 0.50 | 0.80 |
| manoalide* | 0.6 | 0.8 |

*Data for manoalide are provided for comparison.

SPECIFIC EMBODIMENTS

The compounds of the present invention can be made by the synthetic chemical pathways which are illustrated here in general terms, and in the specific examples as well. The synthetic chemist will readily appreciate that the conditions described here in general terms, and specifically, can be generalized to any and all compounds represented by Formula 1. Furthermore, the synthetic chemist will readily appreciate that the herein described steps may be varied or adjusted by those skilled in the art without departing from the scope and spirit of the invention.

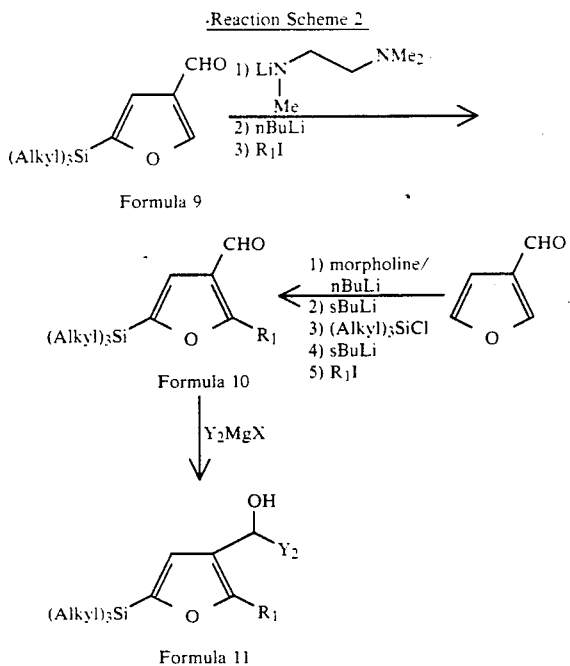

Formula 9

Formula 10

Formula 11

Reaction Scheme 2

Referring now to Reaction Scheme 2, a general process is shown for preparing compounds of the invention which are 5-alkyl or phenyl substituted 5-hydroxy-2-furanone derivatives. The reaction sequence starts with the preparation of the appropriate 5-alkyl (or phenyl) substituted 2-trialkylsilyl-4-furaldehyde (Formula 10). As it becomes fully apparent from the ensuing description of Specific Examples, the 5-alkyl substituted 2-trialkylsilyl-4-furaldehydes (Formula 10) can be prepared from 2-trialkylsilyl-4-furaldehydes (Formula 9) by alkylation with a suitable alkylating agent ($R_1$—I, such as methyl iodide; $R_1$ is generally defined as in connection with Formula 1) in the presence of strong base (such as n-butyl lithium). 2-Trialkylsilyl-4-furaldehydes (Formula 9) can be obtained, for example, in accordance with the teachings of U.S. Pat. No. 4,935,530 the specification of which is incorporated herein by reference. Alternatively, the 5-alkyl substituted 2-trialkylsilyl-4-furaldehydes (Formula 10) can also be obtained from 3-furaldehydes by first introducing the 2-trialkylsilyl substituent, and without isolating the intermediate, thereafter introducing the 5-alkyl group. These reactions are also conducted in the presence of strong base, such as n-butyl and s-butyl lithium and morpholine, as is described specifically in connection with the preparation of 5-methyl-2-triethylsilyl-4-furaldehyde.

2-Trialkylsilyl-5-phenyl-4-furaldehyde is made by introducing the phenyl group into the 5 position of a 2-trialylsilyl-4-furaldehyde (preferable 2-triethylsilyl-4-furaldehyde) with tetrakis (triphenylphosphine) palladium (O) under conditions described in the Specific Examples.

The 5-alkyl (or phenyl) substituted 2-trialkylsilyl-4-furaldehydes (Formula 10) are thereafter reacted with a Grignard reagent of the general formula $Y_2$—Mg—X (where X is halogen and $Y_2$ is defined as in connection with Formula 1) to yield compounds of Formula 11 where the side chain in the 4-position of the furan nucleus is alpha-hydroxy substituted.

The $Y_1$ substituent, (defined in connection with Formula 1) is introduced into the alpha-hydroxy function of the side chain of the structures shown in Formula 11 by alkylation with a suitable alkylating agent (for example of the formula $Y_1$—X where $Y_1$ is alkyl and X is halogen or other suitable leaving group), acylation by a suitable acyl anhydride or acyl halide (for example of the formula $R_3$—CO—X where X is halogen and $R_3$ is defined as in connection with Formula 1), sulphonyl chloride (of the formula $R_3SO_2Cl$ where $R_3$ is defined as in connection with Formula 1) or reaction with an isocyanate (of the formula $CONHR_3$ where $R_3$ is defined as in connection with Formula 1.

The resulting 2-trialkylsilyl-5-alkyl (or phenyl) 4-substituted furans of Formula 12 are converted into the useful compounds of the invention of Formula 13 (where $R_1$, $Y_1$ and $Y_2$ are defined as in connection with Formula 1) by oxydation with singlet oxygen. The conditions of these reactions are described in detail in connection with several specific examples. In general terms, the reactions are preferably conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. The reaction mixture and vessel is flushed with oxygen and the reaction is conducted at low temperature, at approximately −78° C., or at approximately 0° C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

The $Y_3$ substituent, as defined in connection with Formula 1 is introduced into the structure of Formula 13 by alkylation, acylation (for example with acetic anhydride) or other reactions which are per se known in the art.

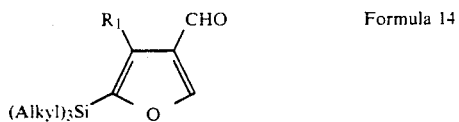

Formula 14

Compounds of the invention which 3-alkyl or phenyl substituted 5-hydroxy-2(5H)-furanone derivatives are prepared from 3-alkyl (or phenyl) substituted 2-trialkylsilyl-4-furaldehydes (Formula 14) by reaction steps similar to those described above in connection with Reaction Scheme 2 relating to conversion of 5-alkyl (or phenyl) substituted 2-trialkylsilyl-4-furaldehydes (Formula 10) into compounds of the invention.

Reaction Scheme 3

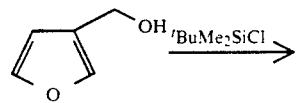

-continued
Reaction Scheme 3

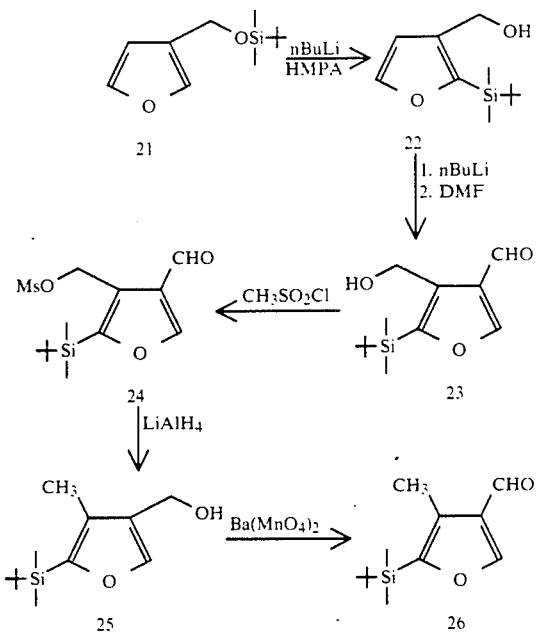

Preparation of 2-trialkylsilyl-3-methyl-4-furaldehydes is illustrated through the preparation of 2-(tert-butyldimethylsilyl)-3-methyl-4-furaldehyde, shown in Reaction Scheme 3. Commercially available 3-furylmethanol (Compound 20) is reacted with tert-butyl-dimethylsilyl chloride to yield 3-(O-tert-butyldimethylsilyl-methoxy)furan (Compound 21). The reaction of Compound 21 with n-butyl lithium in hexamethylphosphoramide (HMPA) and tetrahydrofuran (THF) provides 3-(2-tertbutyldimethsilyl) furylmethanol (Compound 22). Reaction of Compound 22 with n-butyl lithium and dimethylformamide introduces a formyl group into the furan nucleus to yield 2-(tertbutyldimethylsilyl)-3-hydroxymethyl-4-furaldehyde (Compound 23) Compound 23 is then "mesylated" with methane sulfonyl chloride to provide 3-(2-tert-butyldimethylsilyl-4-carbonyl)furylmethyl methanesulfonate (Compound 24) which is reduced (for example with lithium aluminum hydride) to give 4-[2-(tert-butyldimethylsilyl)-3-methyl]furylmethanol (Compound 25). Oxydation of Compound 25 to provide an aldehyde function in the 4-position yields 2-(tert-butyldimethylsilyl)-3-methyl-4-furaldehyde (Compound 26). As is noted above, Compound 26 is converted into the compounds of the invention in a series of reactions which are analogous to the reactions described in connection with the corresponding 5-substituted 2-trialkylsilyl-4-furaldehydes.

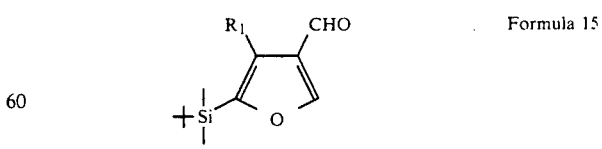

Formula 15

2-Trialkylsilyl-3-alkyl-4-furaldehydes where, unlike in the preceding example, the 3-alkyl group ($R_1$) is other than methyl, can be made in a series of step analogous to synthesizing 2-(tert-butyldimethylsilyl)-3-methyl-4-furaldehyde (compound 26). However, in this case instead of Compound 24 the corresponding para-toluenesulfonate [(3-(2-tert-butyldimethylsilyl-4-carbonyl)-furylmethyl para toluenesulfonate (Compound 27)] is prepared. Compound 27 is then reacted with an organocuprate of the general formula $(R_5)_2$-CuLi to replace the paratoluenesulfonyloxy group with $R_5$, where $R_5$ is an "alkyl" group one carbon shorter than the definition of "alkyl" for $R_1$ in connection with Formula 1. The result of the reaction with organocuprate is a compound of the Formula 15, which is thereafter reacted with a Grignard (or like) reagent followed by introduction of the $Y_1$ group, as described above.

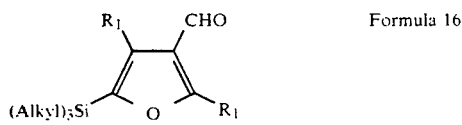

Formula 16

Compounds of the invention which are derivatives of 3,5-dialkyl-5-hydroxy-2-furanone (in Formula 1 n is 2) can be made from 2-trialkylsilyl-2,5-dialkyl-4-furaldehydes (Formula 16) by reactions analogous to the reactions outlined in reaction Scheme 2, i. e. in steps which start with reacting the furaldehyde of Formula 16 with a a Grignard (or like) reagent of the general formula $Y_2$—Mg—X where x is bromine or iodine. The 2-trialkylsilyl-2,5-dialkyl-4-furaldehydes (Formula 16) are prepared in accordance with the invention by alkylating the 2-trialkylsilyl-3-alkyl-4-furaldehydes of Formula 14 with an alkylating agent (such as methyl iodide) in the presence of strong base (such as n-butyl lithium).

num hydride to yield (3-phenyl)-4-furyl-methanol (Compound 53). Compound 53 is oxidized to give 3-phenyl-4-furaldehyde (Compound 54). 3-phenyl-4-furaldehyde (Compound 54) is then reacted with a Grignard (or like) reagent of the formula $Y_2$—Mg—X (X is bromine or iodine) to introduce the $Y_2$ substituent into the compounds of the invention ($Y_2$ is defined as in connection with Formula 1). The resulting 4-(alpha-hydroxy substituted)-3-phenyl furan can be acylated (for example acetylated), reacted with an isocyanate, or otherwise reacted with the appropriate reagent (as described above in connection with Reaction Scheme 2) to introduce the $Y_1$ substituent ($Y_1$ is defined as in connection with Formula 1). In Reaction Scheme 4 Formula 17 illustrates generally the compounds which are obtained by performing the above-noted reactions on Compound 54. Oxidation of the compounds of Formula 17 with singlet oxygen provides a mixture of 4-substituted-3-phenyl-5-hydroxy-2(5H)-furanones (Formula 18) and 3=substituted-4-phenyl-5-hydroxy-2(5H)-furanones (Formula 19).

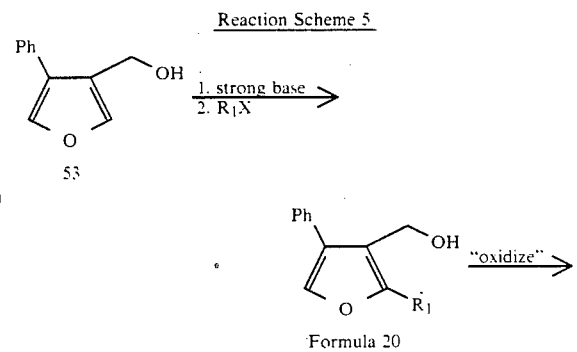

Reaction Scheme 5

Formula 20

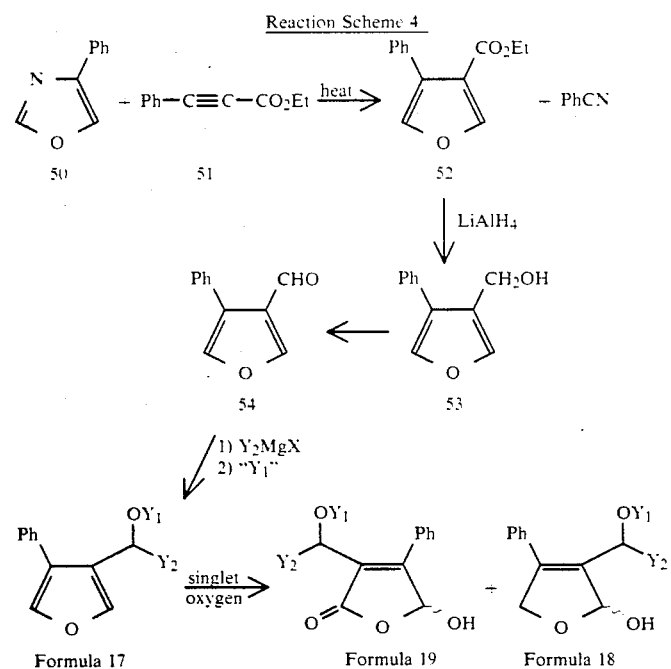

Compounds of the invention which are substituted in the 3-position of the furan nucleus with a phenyl group (in other words where with reference to Formula 1 $R_1$ is in the 3-position and is phenyl) are prepared by the procedure illustrated in Reaction scheme 4. Phenyloxazole (Compound 50) is reacted with ethyl phenyl-prop-1-yn-oate (Compound 51) to yield ethyl 3-phenyl-4-furanoate (Compound 52) and phenyloyanide as a side product. Compound 5z is reduced with lithium alumi- -continued
Reaction Scheme 5

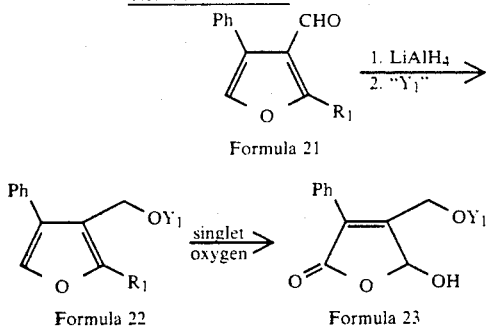

Compounds of the invention which have a phenyl substituent in the 3-position of the furan nucleus, and also have a 5-alkyl substituent are made from the intermediate (3-phenyl)-4-furylmethanol (Compounds 53) as is illustrated in Reaction Scheme 5. Compound 53 is alkylated in the presence of strong base (such as n-butyl lithium) with an alkylating agent (designated $R_1$—X, X is halogen preferably I, and $R_1$ is defined as in connection with Formula 1 except that $R_1$ is not phenyl, or hydrogen) to yield 3-phenyl-5-alkyl-4-furylmethanol (Formula 20). The compounds of Formula 20 can be oxidized to provide a 3-phenyl-5-alkyl substituted 4-furaldehyde (Formula 21). In order to obtain the preferred compounds of this series where, with reference to Formula 1 $Y_2$=H, the furylmethanol of Formula 20 is reacted with an alkylating, acylating, alkylsulfonylating reagent, with an isocyanate or with other appropriate reagent to introduce the $Y_1$ group on the hydroxyl function in the side chain of the 4-position on the furan nucleus. The resulting 4-substituted 3-phenyl-5-alkyl-furyl methanol (Formula 22) which is substituted on the hydroxyl group is subjected to oxidation with singlet oxygen to provide the compounds of the invention where the 5-hydroxy-2(5H)-furanone is substituted with phenyl in the 3-position and with alkyl in the 5-position (Formula 23).

The following examples of specific compounds of the invention, and specific examples of the synthetic steps in which the compounds and certain intermediates are made, are set out to illustrate the invention, not to limit its scope.

SPECIFIC EXAMPLES

2-Trimethylsilyl-4-furaldehyde (Compound 30)

n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°–50°/0.25 torr.

$^1$H NMR (CDCl$_3$): 0.29 (s, 9H), 6.98 (s, 1H), 8.25 (s, 1H) and 9.95 (s, 1H).

$^{13}$C NMR (CDCl$_3$): −2.0, 116.2, 128.9, 155.3, 164.1 and 184.5.

HRMS exact mass calculated for C$_8$H$_{12}$O$_2$Si(M$^+$) 168.0607, found 168.0588. See also U.S. Pat. No. 4,935,530, the specification of which is incorporated herein by reference.

2-Triethylsilyl-4-furaldehyde (Compound 31)

n-Butyl lithium (a 2.5M solution in hexane: 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point 85°–90°/0.4 torr.

IR (neat): 1680cm$^{-1}$ $^1$H NMR (CDCl$_3$): 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$): 2.9, 7.1, 117.2, 128.8, 155.6, 162.3 and 184.6.

HRMS m/e exact mass calculated for C$_{11}$H$_{18}$O$_2$Si(M$^+$) 210.1076, found 210.1071. See also U.S. Pat. No. 4,935,530, the specification of which is incorporated herein by reference.

2-(tert-Butyldimethylsilyl)-4-furaldehyde (Compound 32)

n-Butyl lithium (a 2.5 M solution) in hexane; 8.3 ml, 20.8 mmol) was added to a solution of morpholine (1.81 ml, 20 mmol) in tetrahydrofuran (100 ml) at −780° C. under argon. After 20 minutes 3-furaldehyde (1.8 ml, 20.8 mmol) was added. After another 15 minutes, sec-butyl lithium (a 1.3M solution in cyclohexane; 16.8 ml, 21.9 mmol) was added dropwise and stirring continued at −78° C. for 1 hour before a solution of t-butyldimethylsilyl chloride (9.4 g, 62.4 mmol) in tetrahydrofuran (10 ml) was added. Stirring was continued overnight (16 hours) while the cooling bath was allowed to attain room temperature. The solution was poured into ice cold 10% (v/v) hydrochloric acid (40 ml) and after stirring at 0° for 10 minutes, the layers were separated. The aqueous phase was extracted with diethyl ether. All the organic phases were combined, dried (magnesium sulfate) and evaporated to dryness to give a brown oil, which was distilled under high vacuum to give the title aldehyde. boiling point 80°–5°/0.5 torr., m.p. 37-8.

$^1$H NMR (CDCl$_3$): 0.23 (s, 6H), 0.90 (s, 9H), 6.99 (s, 1H), 8 25 (s, 1H) and 9.94 (s, 1H).

$^{13}$C NMR (CDCl$_3$): 16.6, 26.1, 117.3, 128.8, 155.5, 162.7 and 184.5

HRMS exact mass calculated for $C_{11}H_{18}O_2Si$ ($M^-$) 210.1076, found 210.1075.

5-Methyl-2-trimethylsilyl-4-furaldehyde (Compound 33)

n-Butyl lithium (a 1.6 M solution in hexane; 2.04 ml, 3.28 mmol) was added dropwise to a solution of N,N'N'-trimethylethylenediamine (0.46 ml, 3.56 mmol) in tetrahydrofuran (7 ml) at −78 degrees under argon. After 15 minutes, a solution of 2-trimethylsilyl-4-furaldehyde (Compound 30, 0.5 g, 2.98 mmol) in tetrahydrofuran (2 ml) was added, followed by n-butyl lithium (3.72 ml, 5.94 mmol) after 15 minutes. Iodomethane (1.12 ml, 17.9 mmol) was then added and the mixture was allowed to warm to room temperature gradually over ½ hour. The mixture was quenched with brine and extracted with ethyl ether. Evaporation of the dried (magnesium sulphate) extracts gave an oil, which was purified by flash chromatography using 10% ethyl ether/hexane. Fractions with $R_f$ of about 0.22 on evaporation afforded the title methylfuran as a light yellow oil.

$^1$H NMR ($CDCl_3$): 0.29 (s, 9H), 2.63 (s, 3H), 6.91 (s, 1H) and 9.95 (s, 1H).

LRMS m/e (% abundance). $183^- +1$, 35), 167 (28), 149 (20), 83 (40), 73 (100) and 43 (31).

5-Methyl-4-(1-acetoxytridecyl)-2-trimethylsilylfuran (Compound 34)

A mixture of 1-bromododecane (261 mg, 0.11 mmol) and magnesium turnings (27 mg, 0.11 mmol) in tetrahydrofuran (7 ml) was refluxed under argon for 1 hour. After cooling to room temperature, a solution of 5-methyl-2-trimethylsilyl-4-furaldehyde (Compound 33, 158.6 mg, 0.87 mmol) in tetrahydrofuran (1 ml) was added, followed by acetic anhydride (0.25 ml, 2.6 mmol) after 1 hour. Stirring was continued at room temperature overnight and the mixture was quenched with water. Extraction (ethyl ether) and evaporation of the dried (magnesium sulphate) extracts gave an oil, which was purified by preparative TLC (20×20 cm, 1000 micron silica plate; developed with 5% ethyl ether/hexane). The title ester was obtained as a light yellow oil.

$^1$H NMR ($CDCl_3$) 0.26 (s, 9H), 0.91 (t, 3H, J=6.9 Hz), 1.27 (s, 20H), 1.60-1.90 (m, 2H), 2.05 (s, 3H), 2.35 (s, 3H), 5.69 (t, 1H, J=7.5 Hz) and 6.55 (s, 1H).

LRMS m/e (% abundance): 394 ($M^-$, 8), 352 (23), 334 (36), 183 (47), 167 (20), 117 (28), 73 (100) and 43 (41).

4-(1-Acetoxytridecyl)-5-hydroxy-5-methyl-2-furanone (Compound 1)

A mixture of 5-methyl-4-(1-acetoxytridecyl)-2-trimethylsilylfuran (Compound 34, 237 mg, 0.60 mmol) and Rose Bengal (5 mg) in tetrahydrofuran (10 ml) was exposed to singlet oxygen at −78 degrees C. for 2 hours. The residue, after solvent removal, was purified by preparative TLC (20×20 cm, 1000 micron silica plate; developed with 60% ethyl ether/hexane). The title furanone was obtained as a light yellow oil. This compound is a mixture of epimers which isomerizes upon standing.

$^1$H NMR ($CDCl_3$): 0.92 (t, 3H, J=6.9 Hz), 1.30 (brs, 20H), 1.70 (brs, 3H), 1.80 (m, 2H), 2.15 (2s, 3H), 5.25 (brm, 1H), 5.45 (t, 0.7H, J=7.5 Hz), 5.96 (s, 0.7H), 6.03 (s, 0.3H) and 6.11 (brm, 0.3H).

$^{13}$C NMR ($CDCl_3$) 13.7, 20.5, 22.3, 23.3, 24.1, 24.9, 28.8, 29.0, 29.1, 29.2, 29.3, 31.6, 33.2, 33.3, 69.0, 69.3, 106.5, 117.0, 118.1, 169.6, 169.7, 169.8, 170.0, 170.1, 170.7, 171.9 and 172.0.

HRMS exact mass calculated for $C_{20}H_{38}NO_5$ $(M+NH_4)^-$ 372.2749, found 372.2754.

3-(O-tert-Butyldimethylsilylmethoxy)furan (Compound 21)

3-Furylmethanol (15.5 ml, 0.18 mol), followed by 1,8-diazabicyclo[5.4.0]undec-7-ene (29.7 ml, 0.19 mol) was added to solution of tert-butyldimethylsilyl chloride (29.9 g, 0.19 m) in dichloromethane (140 ml) at 0 degrees C. under argon. After stirring at room temperature overnight, the reaction was quenched with 5% ice cold hydrochloric acid. Extraction with dichloromethane and evaporation of the dried (magnesium sulfate) extracts gave an oil which was purified by flash chromatography on silica using hexane to give the desired silyl ether.

$^1$H NMR ($CDCl_3$): 0.05 (s, 6H), 0.89 (s, 9H), 4.58 (s, 2H), 6.35 (1H) and 7.33 (m, 2H).

3-(2-tert-Butyldimethylsilyl)furylmethanol (Compound 22)

n-BuLi (a 1.5 M solution in hexane; 38.9 ml, 58 mmol) was added to a solution of 3-(O-tert-butyldimethylsilylmethoxy)furan (Compound 21, 11.2 g, 52.7 mmol) and hexamethylphosphoramide (10.1 ml, 58 mmol) in tetrahydrofuran (200 ml) at −78 degrees C. under argon. After 1 hour stirring at −20 degrees C., the reaction was quenched with an aqueous solution of saturated ammonium chloride. Extraction (ethyl acetate) and evaporation of the dried (magnesium sulfate extracts gave an oil, which was purified by flash chromatography on silica using 20% ethylacetate/hexane to give the desired furylmethanol.

$^1$H NMR ($CDCl_3$): 0.29 (s, 6H), 0.90 (s, 9H), 1.45 (brt, 1H), 4.59 (d, 2H, J=3.4 Hz), 6.49 (d, 1H, J=1.7 Hz) and 7.60 (d, 1H, J=1.7 Hz).

2-(tert-Butyldimethylsilyl)-3-hydroxymethyl-4-furaldehyde (Compound 23)

n-BuLi (a 1.6 M solution in hexane; 2.7 ml, 4.28 mmol) was added dropwise to a solution of 3-(2-tert-butyldimethylsilyl)furylmethanol (Compound 22, 430 mg, 2.0 mmol) in dimethoxyethane (5 ml) at −78 degrees C. under argon. After stirring at 0 degrees C. for 15 minutes, lithium chloride (860 mg, 20.4 mmol), followed by N,N-dimethylformamide (0.35 ml, 4.48 mmol) was added. Stirring continued at 0 degrees C. for 16 hours and the mixture was quenched with ammonium chloride. Extraction with ethyl acetate and evaporation of the dried (magnesium sulfate) extracts gave a solid, which was recrystallized from hexane to give the titled aldehyde.

IR ($CHCl_3$): 3470, 1680, 1660, 1570 and 1510.

$^1$H NMR ($CDCl_3$): 0.28 (s, 6H), 0.87 (s, 9H), 4.08 (t, 1H, J =7.3 Hz), 4.58 (d, 2H, J=7.3 Hz), 8.27 (s, 1H) and 9.90 (s, 1H).

$^{13}$CNMR ($CDCl_3$): 5.9, 17.1, 26.1, 55.4, 128.3, 133.9, 158 2, 158.3 and 186.6.

LRMS m/e (% abundance): 258 [$(M+NH_4)^+$,1], 240 (56), 223 (53), 184 (26), 183 (10) and 167 (41).

4-[2-(tert-Butyldimethylsilyl)-3-methyl]furylmethanol (Compound 25)

a) 3-(2-tert-Butyldimethylsilyl-4-carbonyl)furylmethyl methanesulfonate (Compound 24)

A solution of 2-(tert-butyldimethylsilyl)-3-hydroxymethyl-4-furaldehyde (Compound 23, 4.98 g, 20.7 mmol), diisopropylethylamine (7.95 ml, 45.6 mmol) in tetrahydrofuran (70 ml) was added dropwise to a solution of methanesulfonyl chloride (6.42 ml, 82.9 mmol) in tetrahydrofuran (70 ml) at −20 degrees C. under argon. After stirring at −20 degrees C. for 90 minutes, the mixture was diluted with ethyl ether and washed successively with 10% hydrochloric acid, water and brine. Evaporation of the dried (magnesium sulfate) organic phase gave an oil, which was purified by flash chromatography on silica using 20% ethylacetate/hexane to give the titled mesylate.

'HNMR (CDCl$_3$): 0.36 (s, 6H), 0.93 (s, 9H), 3.16 (s, 3H), 5.33 (s, 2H), 7.27 (s, 1H), 8.26 (s, 1H) and 10.02 (s, 1H).

b) 4-[2-(tert-Butyldimethylsilyl)-3-methyl]furylmethanol (Compound 25)

Lithium aluminum hydride (a 1.0 M solution in THF: 62.2 ml, 62.2 mmol) was added dropwise to a solution of the mesylate (Compound 24) from above in THF (10 ml) at −20 degrees C. under argon. After 20 minutes, TLC showed that the reaction has been completed. The mixture was quenched carefully with dilhydrochloric acid. Extraction with diethyl ether and evaporation of the dried (magnesium sulfate) extracts gave an oil, which was purified by flash chromatography on silica using 20% ethylacetate/hexane to give the titled alcohol.

IR (CHCl$_3$): 3450 and 1600.

'HNMR (CDCl$_3$): 0.27 (s, 6H), 0.91 (s, 9H), 2.12 (s, 3H), 4.53 (s, 2H) and 7.56 (s, 1H).

$^{13}$CNMR (CDCl$_3$): −6.1, 9.0, 17.5, 26.2, 55.4, 125.5, 130.8, 144.6 and 155.1.

LRMS m/e (% abundance): 226 (M$^-$, 32), 209 (45), 170 (18), 169 (91), 142 (13), 141 (100), 101 (10) 97 (41), 75 (93) and 73 (22).

2-(tert-Butyldimethylsilyl)-3-methyl-4-furaldehyde (Compound 26)

A solution of 4-[2-(tert-butyldimethylsilyl)-3-methyl]-furyl-methanol (Compound 25, 380 mg, 1.68 mmol) in dichloromethane (5ml) was added to a suspension of barium permanganate (6.45 g, 25.2 mmol) in dichloromethane (40 ml) at 0 degrees C. under argon. After stirring at room temperature for 15 hours, the mixture was filtered through celite. After concentration by evaporation, the filtrate was purified by flash chromatography on silica using 5% ethyl ether/hexane to give the titled aldehyde.

IR (CHCl$_3$): 2820, 2740 and 1680

'HNMR (CDCl$_3$): 0.2 (s, 6H), 0.82 (s, 9H), 2.23 (s, 3H), 8.09 (s, 1H) and 9.91 (s, 1H).

$^{13}$CNMR (CDCl$_3$):−6.3, 9.8, 17.3, 25.9, 128.1, 129.9, 156.8, 157.6 and 185.7.

LMRS m/e (% abundance): 224 (11), 158 (16), 167 (100), 83 (12) and 73 (11).

4-(1-Acetoxytridecyl)-2-(tert-butyldimethylsilyl)-3-methylfuran (compound 35)

2-(tert-Butyldimethylsilyl)-3-methyl-4-furaldehyde (Compound 26, 95 mg, 0.42 mmol) was added to a solution of dodecylmagnesium bromide (a 1.0 M solution in THF; 0.51 ml, 0.51 mmol) in THF (1 ml) at 0 degrees C. under argon. When all the aldehyde has reacted, acetic anhydride (80 microliter, 0.85 mmol) was added. After stirring at room temperature for 16 hours, the mixture was quenched with dilute hydrochloric acid. Extraction with diethyl ether and evaporation of the dried (magnesium sulfate) extracts gave an oil, which was purified by flash chromatography on silica using 5% ethyl ether/hexane to give the titled acetate.

IR (CHCl$_3$): 1730 and 1710.

'HNMR (CDCl$_3$): 0.26 (s, 6H), 0.88 (t, 3H, J=6.9 Hz), 1.25 (brs, 20H), 1.80 (m, 2H), 2.03 (s, 3H), 2.07 (s, 3H), 5.78 (t, 1H, J=7.0 Hz) and 7.52 (s, 1H), $^{13}$CNMR (CDCl$_3$): −6.1, 9.5, 13.8, 17.5, 21.0, 22.5, 25.4, 26.2, 29.1, 29.2, 29.3, 29.4, 31.7, 34.6, 68.4, 125.4, 130.2, 144.4, 154.7 and 170.7, LRMS m/e (% abundance):436(M$^+$, 4), 320 (3), 211 (14), 118 (10), 117 (100), 75 (22) and 73 (18).

4-(1-Acetoxytridecyl)-3-methyl-5-hydroxy-2(5H)-furanone (Compound 2)

A mixture of 4-(1-acetoxytridecyl)-2-(tertbutyldimethylsilyl 3-methylfuran (Compound 35, 132 mg, 0.3 mmol), water (a few drops) and Rose Bengal (5 mg) in acetone (30 ml) was exposed to singlet oxygen at 0 degrees C. for 6 hours. The residue, on evaporation, was purified by flash chromatography on silica using 20% ethylacetate/hexane to give the titled furanone.

IR(CHCl)$_3$: 3400, 1780, 1750 and 1730.

$^1$HNMR (CHCl$_3$): 0.82 (t, 3H, J=6.9 Hz), 1.20 (brs, 20H), 1.75 (m, 2H), 1.85 (s, 3H), 2.03 (s, 3H), 2.06 (s, 3H), 5.35 (m, 2H), 5.88 (brs, 1H) and 6.08 (brs, 1H).

$^{13}$C NMR (CDCl$_3$)9.2, 14.2, 20 8, 22.8, 25.6, 29.4, 29.5, 29.6, 29.7, 29.8, 32.1, 32.8, 70.1, 70.7, 97.7, 128.5, 128.9, 156.5, 156.6, 171.7, 172.1, 172.7 and 173.1.

LRMS m/e (% abundance):355 (M$^+$, 16), 296 (11), 295 (59), 294 (100), 277 (19), 267 (45), 126 (34), 125 (41), 112 (18), 95 (23), 81 (22) and 69 (27).

2-(tert-butyldimethylsilyl)-3-methyl-4-(1-phenylcarbamolyoxy) tridecylfuran (Compound 36) and 2-(tert-butyldimethylsilyl)-3-methyl-4-[1-N-phenyl-N-phenylcarbamoyl)carbamoyloxy]tridecylfuran (Compound 37)

Dodecylmagnesium bromide (a 1.0 M solution in THF; 0.89 ml, 0.89 mmol) was added to a solution of 2-tert-butyldimethylsilyl-3-methyl-4-furaldehyde (Compound 26, 200 mg, 0.89 mmol) in THF (5 ml) at 0 degrees C. under argon. After stirring at room temperature for 1 hour, the mixture was re-cooled to 0 degrees C. and phenylisocyanate (97 microliter, 0.89 mmol) was added. Stirring was continued for 5 minutes and the reaction mixture was quenched with ammonium chloride. Extraction with diethyl ether and evaporation of the dried (magnesium sulfate) extracts gave an oil. The crude product was purified by flash chromatography (SiO$_2$; 5% ethylether/hexane) to give the desired mono- and bis-phenylcarbonate. 2-(tert-Butyldimethylsilyl)-3-methyl-4-(1-phenylcarbamoyloxy)tridecylfuran (Compound 36): R$_f$ (5% diethyl ether/hexane): 0.34; IR (CHCl$_3$): 3430, 1725, 1680, 1595 and 1515; 'HNMR (CDCl$_3$): 0.24 (s, 6H), 0.88 (t+s, 12H), 1.23 (m, 20H), 1.90 (m, 2H), 2.09 (s, 3H), 5.77 (t, 1H, J=7.0 Hz), 6.65 (s, 1H), 7.02 (t, 1H, J−7.3 Hz), 7.25 (m, 2H), 7.35 (m, 2H) and 7.54 (s, 1H); $^{13}$CNMR (CDCl$_3$): −6.1, 9.6, 13.8, 17.5, 22.4, 25.4, 26.2, 29.1, 29.2, 29.3, 29.4, 31.7, 34.8, 69.5, 118.7, 123.5, 125.4, 129.2, 130.2, 138.2, 144.4, 153.4 and 154.9.

2-(tert-Butyldimethylsilyl)-3-methyl 4-[1-(N-phenyl-N-phenylcarbamoyl)carbamoyloxy]tridecylfuran (Compound 37): R$_f$(5% diethylether/hexane):0.23; 'H NMR (CDCl$_3$):0.24 (s, 6H), 0.87 (s+t, 12H), 1.24 (m, 20H), 1.56 (m, 2H), 1.79 (s, 3H), 5.75 (t, 1H, J=6, 2Hz), 7.07 (t. 1H. J = 8.0 Hz). 7.20 (m 2H), 7.30 (m, 3H). 7.42 (m, 3H), 7.54 (m, 2H) and 10.9 (s, 1H); $^{13}$CNMR (CDCl$_3$):−6.2. −6.1, 9.3, 13.6, 17.5, 22.4, 24.9, 26.1, 28.8, 29.1, 29.2, 29.3, 29.4, 31.7, 34.4, 72.8, 120.0, 124.0, 124 1, 128.4, 128.9, 129.0, 129.5, 137.4, 138.0, 144.3, 151.8, 155.3 and 155.6.

5-Hydroxy-3-methyl-4-(1-phenylcarbamoyloxy)-tridecyl)-(2(5H)furanone (Compound 3)

A mixture of 2-(tert-butyldimethylsilyl)-3-methyl-4-(1-phenylcarbamoyloxy) tridecylfuran (Compound 36, 226 mg, 0.44 mmol), water ( a few drops) and polymer bound Rose Bengal (0.077 g) in acetone (80 ml) was exposed to singlet oxygen at 0 degrees C. for 5 hours. The residue, on evaporation, was purified by flash chromatography (SiO$_2$, 20% ethylacetate/hexane) to give the titled furanone. IR (CHCl$_3$): 3400–3200, 1768, 1725, 1605 and 1520; 'HNMR (CDCl$_3$): 0.88 (t, 3H, J = 6.9 Hz), 1.26 (m, 20H), 1.80 (m, 1H), 1.91 (s, 3H), 1.95 (m, 1H), 5.48 (brt, 1H), 5.52 (m, 1H), 5.95 (br, 1H), 6.04 (brs, 1H), 6.19 (brs, 1H), 7.00–7.40 (m, 6H); $^{13}$C NMR (CDCl$_3$):8.7, 13.8, 22.4, 25.2, 28.9, 29.1, 29.2, 29.3, 29.4, 29.5, 31.7, 32.4, 32.5, 69.9, 70.6, 97.2, 97.4, 118.8, 119.0, 119.4, 123.9, 124.1, 128.1, 128.9, 129.2, 137.3, 137.6, 153.2, 153.4, 153.6, 156.0, 156.8, 172.5 and 172.7.

5-Methy-2-triethylsilyl-4-furaldehyde (Compound 38)

n-Butyl lithium (a 1.6 M solution in THF; 19.0 ml. 30.4 mmol) was added to a solution of morpholine (2.67 ml. 30.4 mmol) in THF (20 ml) at −78 degrees C. under argon. After 20 minutes, 3-furaldehyde (1.8 ml, 28.9 mmol) was added, followed by s-butyl-lithium (a 1.3 M solution in cyclohexane; 23.4 ml, 30.4 mmol) after another 20 minutes. Stirring was continued for 2 hours and chlorotriethylsilane (5.1 ml, 30.4 mmol) was added. After 2 hours at −78 degrees C., s Buli (23.4 ml. 30.4 mmol) was added, followed by iodomethane (5.4 ml, 86.9 mmol) after another 2 hours. The mixture was stirred at room temperature for 15 hours and quenched with ice cold dilute hydrochloric acid. Extraction with diethylether and evaporation of the dried (magnesium sulfate) extracts gave an oil, which was purified by flash chromatography on silica using 10% diethyl ether/hexane to give the titled aldehyde.

IR (CHCl$_3$): 1690.

'HNMR (CDCl$_3$): 0.75 (q, 6H, J = 8.0 Hz), 0.98 (t, 9H, J = 8.0 Hz), 2.60 (s, 3H), 6.90 (s, 1H) and 9.90 (s, 1H).

$^{13}$CNMR (CDCl$_3$): 2.6, 6.7, 12.5, 118.8, 122.8, 158.5, 166.2 and 185.1; HRMS exact mass calculated for C$_{12}$H$_{20}$O$_2$S$_i$ 224.1232 found 224.1226

4-(1-Acetoxytridecyl)-5-methyl-2-triethylsilylfuran (Compound 39)

5-Methyl-2-triethylsilyl-4-furaldehyde (Compound 38, 145 mg, 0.65 mmol) was added to a solution of dodecylmagnesium bromide (a 1.0 M solution in THF; 0.76 ml, 0.74 mmol) in THF at 0 degrees C. under argon. When all the aldehyde has consumed, acetic anhydride (0.1 6 ml, 1.71 mmol) was added. Stirring was continued at room temperature for 15 hours and the mixture was quenched with water. Extraction with diethyl ether and evaporation of the dried (magnesium sulfate) extracts gave an oil, which was purified by flash chromatography on silica using 5% diethyl ether/hexane to give the titled acetate.

IR (CHCl$_3$): 1730

'HNMR (CDCl$_3$):0.75 (q, 6H, J = 8.0 Hz), 0.88 (t, 3H. J = 7.0 Hz), 0.95 (t, 9H, J = 8.0 Hz), 1.25 (brs, 20H), 1.75 (m, 1H), 1.95 (m, 1H), 2.01 (s, 3H), 2.31 (s, 3H), 5.69 (t, 1H, J = 7.2 Hz) and 6.55 (s, 1H).

$^{13}$CNMR (CDCl$_3$):−2.9, 7.0, 11.9, 13.8, 21.0, 22.5, 25.3, 25.7, 29.0, 29.2, 29.3, 29.4, 31.7, 34.8, 68.8, 118.8, 120.3, 154.1, 156.1 and 170.7. LRMS m/e (% abundance) 436 (M$^−$, 9), 377 (22), 376 (33), 347 (43), 239 (29), 145 (100), 115 (34), 103 (30) and 87 (30); HRMS Exact Mass Calculated For C$_{26}$H$_{48}$O$_3$Si (M$^+$) 43 6.3373, found 436.3374.

4-(1-Acetoxytridecyl)-5-hydroxy-5-methyl-2-furanone (Compound 1)

A mixture of 4-(1-acetoxytridecyl)-5-methyl-2-triethylsilylfuran (compound 39, 231 mg, 0.53 mmol), water (a few drops) and Rose Bengal (6.3 mg) in acetone (100 ml) was exposed to singlet oxygen at 0 degrees C. for 3 hours. The residue, after evaporation, was purified by flash chromatography on silica using 10% ethylacetate/hexane to give the titled furanone. This compound is a mixture of epimers which isomerizes upon standing.

IR (CHCl3): 3600–3200, 1770 and 1740.

For further physical data of Compound 1 see the description of preparing the compound from Compound 34.

5-Methyl-2-triethylsilyl-4-(1-phenylcarbamoyloxy)-tridecylfuran (Compound 40)

A solution of 5-methyl-2 triethylsilyl-4-furaldehyde (Compound 38, 219 mg, 0.98 mmol) in THF (5 ml) was added to a solution of dodecylmagnesium bromide (a 1.0 M solution in THF; 1.08 ml; 1.08 mmol) in THF at 0 degrees C. under argon. When all the aldehyde was consumed, phenylisocyanate (0.12 ml, 1.08 mmol) was added. After stirring at room temperature for 16 hours, the mixture was quenched with dilute hydrochloric acid. Extraction with diethyl/ether and evaporation of the dried (magnesium sulfate) extracts gave an oil, which was purified by flash chromatography on silica using 5% diethyl/ether/hexane to give the titled furan.

IR (CHCl$_3$):3440, 1730 and 1520.

'HNMR (CDCl$_3$):0.72 (q, 6H, J = 6.6 Hz), 0.88 (t, 3H, J = 6.6 Hz), 0.98 (t, 9H, J = 6.6 (Hz), 1.25 (brs, 20H), 1.75 (m, 1H), 1.95 (m, 1H), 2.36 (s, 3H), 5.70 (t, 1H, J = 7.3 Hz). 6.57 (s, 1H), 6.62 (br, 1H), 7.02 (m, 1H), 7.29 (m, 2H) and 7.37 (m, 2H).

$^{13}$CNMR (CDCl$_3$):2.9, 7.1 11.9, 13.8, 22.5, 25.3, 29.1, 29.2, 29.3, 29.4, 31.7, 35.0, 69.9, 118.7, 118.8, 120.2, 123.3, 129.1, 138.3, 144.8, 153.5, 154.3 and 156.3.

5-Methyl-5-hydroxy-4-(1-phenylcarbamoyloxy)tridecyl-2-furanone (Compound 4)

A mixture of 5-methyl-2-triethylsilyl-4-(1-phenylcarbamoyloxy) tridecylfuran (Compound 40, 80 mg, 0.13 mmol) water (a few drops) and Rose Bengal (ca, 3 mg) in acetone (60 ml) was exposed to singlet oxygen at 0 degrees C. for 4 hours. The residue, after evaporation, was purified by flash chromatography on silica using 20% ethylacetate/hexane to give the titled furanone.

IR (CHCL$_3$):3440, 3400–3240, 1765, 1730, 1600 and 1525.

'HNMR (CDCl$_3$): 0.88 (t, 3H, J −6.9 Hz), 1.26 (brs, 20H), 1.67 (brm, 2H), 1.79 (brs, 3H), 5.18 (brm, 1H), 5.50 (brm, 1H), 5.85 (br, 1H), 6.03 (br, 1H), 7.12 (m, 2H) and 7.40 (m, 3H).

$^{13}$CNMR (CDCl$_3$): 13.8, 22.4, 22.8, 24.2, 24.3, 24.8, 25.1, 28.9, 29.1, 29.2, 29.3, 29.4, 31.7, 3.33, 34.0, 69.6, 70.2, 70.3, 98.2, 106.5, 118.1, 119.2, 124.1, 124.3, 124.5, 129.3, 136.9, 153.9, 169.9 and 170.4.

LRMS m/e (% abundance):431 (M+, 4), 277 (7), 153 (6), 137 (12), 126 (12), 119 (25), 109 (11), 94 (13), 93 (100) and 55 (30).

5-butyl-2-triethylsilyl-4-furaldehyde (Compound 41)

Using the same procedure as for 5-methyl-2-trimethylsilyl-4-furaldehyde but substituting 2-trimethylsilyl-4-furaldehyde (Compound 30) and methyl iodide with 2-triethylsilyl-4-furaldehyde (Compound 31) and 1-iodobutane, respectively, gives 5-butyl-2-triethylsilyl-4-furaldehyde (Compound 41). IR (neat): 1690 cm−1; $^1$HNMR (CDCl$_3$):0.73 (q, 6H, J=8.4 Hz), 0.95 (m, 12H), 1.36 (p, 2H, J=7.5 Hz), 1.69 (p, 2H, J=7.5 Hz), 2.94 (t, 2H, J=7.5 Hz), 6.89 (s, 1H) and 9.91 (s, 1H) $^{13}$CNMR (CDCl$_3$): 3.03, 7.17, 13.6, 22.2, 26.8, 30.4, 118.6, 122.5 158.4, 170.2 and 184.8. LRMS m/e (% abundance):266 (M+, 20) 238 (20) 237 (100), 87 (10) and 75 (20); HRMS exact mass calculated for $C_{15}H_{26}O_2Si$ 266.1702, found 266.1690.

5-Butyl-5-hydroxy-4-(1-phenylcarbamoyloxy)tridecyl-2-furanone (Compound 5)

a) 5-Butyl-4-(1-phenylcarbamoyloxy)tridecyl-2-triethylsilylfuran (Compound 42)

Dodecyl magnesium bromide (a 1.0 M solution in THF; 0.25 ml, 0.25 mmol) was added to a solution of 5-butyl-2-triethylsilyl- 4-furaldehyde (Compound 41, 59 mg, 0.22 mmol) in TUF (1 ml) at 0 degrees C. under argon. When all the aldehyde has reacted, phenylisocyanate (27 microliter, 0.25 mmol) was added and stirring was continued at −40 degrees C. for 14 hours. Without purification the crude product was used in the next step.

$^1$HNMR (CDCl$_3$)

b) 5-Butyl-5-hydroxy-4-(1-phenylcarbamoyloxy)tridecyl-2-furanone (Compound 5)

Water (a few drops) and Rose Bengal (ca. 3 mg) were added to the above reaction mixture. The mixture was exposed to singlet oxygen for 3 hours at 0 degrees C. The residue, after evaporation, was purified by preparative TLC (SiO$_2$) developed with 40% diethylether/hexane to give the titled furanone. IR (CHCl$_3$):3600–3240, 3440, 1770, 1730, 1605, 1550 and 1530. $^1$HNMR (CDCl$_3$): 0.88 (m, 6H), 1.30 (brm, 22H), 1.50 (m, 2H), 1.75 (m, 2H), 2.00 (m, 2H), 5.10 (brm, 1H), 5.70 (br, 1H), 6.04 (brs, 1H), 6.95 (brs, 1H), 7.15 (brm, 1H), 7.30 (m, 3H) and 7.50 (m, 2H)

$^{13}$C NMR (CDCl$_3$) 13.6, 13.8, 22.1, 2.22, 22.4, 24.3, 24.6, 25.1, 28.6, 28.9, 29.0, 29.1, 29.3, 29.4, 31.7, 32.9, 33.5, 36.3, 69.7, 108.3, 118.9, 119.2, 119.4, 120.2, 124.5, 128.6, 129.0, 129.2, 129.3, 129.4, 136.8, 169.2, 169.7 and 169.9. LRMS m/e (% abundance): 491[(M+NH$_4$)+, 67], 474[(M+H)+, 86], 473 (M+, 23), 456 (33), 372 (30), 354 (30), 337 (66), 319 (38), 272 (48), 213 (80), 120 (27) 119 (45), 94 (58) and 93 (100).

2-tert-Butyldimethylsilyl-3,5-dimethyl-4-furaldehyde (Compound 43)

Treatment of 2-tert-butyldimethylsilyl-4-hydroxymethyl-3-methylfuran (Compound 25) with n-butyl lithium and iodomethane gives 2-tert-butyldimethylsilyl-3,5-dimethyl-4-hydroxymetylfuran (Compound 44). Oxydation of this furan with barium permanganate gives the titled furaldehyde.

2-Triethylsilyl-5-chenyl-4-furaldehyde. (Compound 47)

Treatment of 2-triethylsilyl-4-furaldehyde (Compound 31) with lithio N,N,N′-trimethylethylenediamine. followed by phenyl trifluoromethanesulfonate in the presence of anhydrous zinc chloride and tetrakis (triphenylphosphine) palladium. (O) provides the titled aldehyde.

4-(1-Acetoxytridecyl)-5-hydroxy-5-phenyl-2-furanone(-Compound 48)

The title compound is prepared through the reaction steps described in Reaction Scheme 2 from 2-triethylsilyl-5phenyl-4-furaldehyde (Compound 47).

5-Hydroxy-5-phenyl-4-(1-phenylcarbamoyloxy)-tridecyl)-2-furanone (Compound 49)

The title compound is prepared through the reaction steps described in Reaction Scheme 2 from 2-triethylsilyl-5-phenyl-4-furaldehyde (Compound 47). Ethyl-4-phenyl-3-furoate (Compound 52) (Adapted from: Liotta, D.; Saindane, M.; Ott, W. Tet. Lett. (1983) 24, 2473.)

A mixture of 4-phenyloxazole (Compound 50, 500 mg, 3.45 mmol) and ethyl phenyl propiolate (Compound 41, 630 mg, 3.62 mmol) were heated in a sealed tube for 16 hours at 210 degrees with stirring. The residue was filtered through silica using 5% ethyl ether/hexanes to give the titled oxazole, 664 mg of a pale oil, which was used without further purification. The starting 4-phenyloxazole was prepared according to Bredereck, H.; Gompper, R. Chem. Ber. (1945), 87, 700.

4-Phenyl-3-furan methanol (Compound 53)

LiAlH$_4$ (1.0 M solution in hexane 1.14 ml, 1.14 mmol) was added dropwise to a solution of ethyl-4-phenyl-3-furoate (Compound 52, 246 mg, assumed 1.28 mmol) in tetrahydrofuran (20 ml) at 0 degrees under argon. The solution was stirred and was allowed to warm to room temperature gradually over ½ hour. The mixture was quenched with saturated ammonium chloride and the organics were extracted into ethyl ether, and washed with H$_2$O. Evaporation of the dried (magnesium sulfate) extracts gave an oil, which was purified by flash chromatography on silica using 20% ethyl acetate/hexanes. This was further purified by recrystallation (hexane/ethyl ether) to give the title compound as pale yellow crystals.

IR (CHCl$_3$): 3600 v. br., 3000 cm$^{-1}$.

$^1$H NMR (CDCl$_3$): 1.90 (brs, 1H), 4.60 (brs, 2H), 7.22 to 7.60 (m, 7H).

$^{13}$C NMR (CDCl$_3$): 55.4, 124.1, 126.4, 127.4, 127.9, 128.9, 132.2, 140.4, 142.3.

HRMS: exact mass calculated for $C_{11}H_{10}O_2(M^+)$ 174.0680, found 174.0696.

4-Phenyl-3-furaldehyde (Compound 54)

A mixture of 4-phenyl-3-furanmethanol (Compound 53, 458 mg, 2.63 mmol), powdered 4A molecular sieves (500 mg), 4-methyl-morpholine-N-oxide (462 mg, 3.95 mmol) and tetrapropylammonium perruthenate (46 mg, 0.13 mmol) in anhydrous dichloromethane (40 ml) were stirred at room temperature for 3 hours. Residue was filtered through silica and concentrated to a brown oil which was purified by flash chromatography on silica using 10% ethyl ether/hexanes to give the titled aldehyde.

IR (CHCl$_3$): 3020, 1690 cm$^{-1}$.

$^1$H NMR (CDCl$_3$) 7.30 to 7.55 (m, 5H); 7.59 (d, J−1.6 Hz, 1H); 8.15 d, J=1.6 Hz, 1H); 9.94 (s, 1H).

$^{13}$C NMR (CDCl$_3$): 125.8, 126.1, 128.0, 128.6, 128.7, 130.0, 142.0, 152.6, 185.2.

HRMS: exact mass calculated for $C_{11}H_8O_2(M^+)$ 172.0524 observed 172.0520.

3(-1-Acetoxytridecyl)-4-phenylfuran (Compound 55)

Dodecylmagnesium bromide (a 1.0 M solution in THF; 2.11 ml, 2.11 mmol) was added to a solution of 4-phenyl-3-furaldehyde (Compound 54, 303 mg, 1.76 mmol) in THF at 0 degrees under argon and gradually allowed to warm to room temperature with stirring. When all of the aldehyde was consumed acetic anhydride (719 mg, 7.04 mmol) was added and stirring was continued for 2 hours more. The reaction was quenched with saturated ammonium chloride and the organics were extracted into ethyl ether. The combined fractions were washed with saturated sodium bicarbonate, water and brine, dried over magnesium sulfate and concentrated to a yellow oil which was purified by flash chromatography on silica using 3% ethyl ether hexanes to give the title compound.

IR (CHCl$_3$): 3020, 1725 cm$^{-1}$.

$^1$H NMR (CDCl$_3$): 0.88 (t, J=6.6 Hz, 3H); 1.10 to 1.40 (m, 20H); 1.53 to 1.78 (m, 2H); 2.00 (s, 3H); 5.92 (t, J=6.8 Hz, 1H); 7.27 to 7.46 (m, 7H).

$^{13}$C NMR (CDCl$_3$): 13.8, 20.9, 22.4, 25.1, 28.9, 29.1, 29.26, 29.36, 29.41, 31.7, 34.4, 68.5, 124.6, 126.3, 127.4, 128.6, 128.8, 132.4, 140.6, 141.5, 170.5.

HRMS: exact mass calculated for $C_{25}H_{36}O_3$ (M$^+$) 384.2667, observed 384.2672.

4-(-1-Acetoxytridecyl)-5-hydroxy-3-phenyl-2(5H)-furanone (Compound 56)

3-(-1-Acetoxytridecyl)-5-hydroxy-4-phenyl-2(5H)-furanone (Compound 57)

A mixture of 3-(-1-acetoxytridecyl)-4-phenylfuran (Formula 17, 506 mg, 1.32 mmol), water (a few drops) and Rose Bengal on polymer beads (1.6 g) in THF was exposed to singlet oxygen at 0 degrees C. for 3 hours. The Rose Bengal was filtered off and the residue was concentrated to a pink oil which was purified by flash chromatography on silica using 5 to 20% ethyl acetate/hexanes to give the title furanones as a mixture of isomers. The isomers were separated by HPLC chromatography on reverse phase Vydac column using 15% water/acetonitrile.

3-(-1-acetoxytridecyl)-5-hydroxy-4-phenyl-2(5H)-furanone (retention time: 26.3 minutes).

IR (CDCl$_3$): 3020, 1760 cm$^{-1}$.

$^1$H NMR (CDCl$_3$): 0.88 (t, J=6.7 Hz, 3H); 1.15 to 1.45 (m, 20H); 1.83 (s, 3H); 1.77 to 1.92 (m, 1H); 1.92 to 2.07 (m, 1H); 5.59 (d, J=5.4 Hz 0.5 H); 5.62 (d, J=5.4 Hz, 0.5 H); 6.31 (s, 1H); 7.40 to 7.54 m(5H).

$^{13}$C NMR (CDCl$_3$): 13.9, 20.3, 22.5, 25.4, 28.9, 29.16, 29.23, 29.34 29.41, 29.45, 31.7, 32.6, 68.9, 97.6, 128.5, 128.7, 128.9, 130.2, 130.4, 157.9, 169.6, 171.1.

LRMS m/z calculated for $C_{25}H_{40}O_5$(M+NH$_4$)=434. Observed 434.

4-(-1-acetoxytridecyl)-5-hydroxy-3-phenyl-2(5H)-furanone (retention time 28.0 minutes).

IR (CHCl$_3$): 3010, 1765 (v. br.)cm$^{-1}$.

$^1$H NMR (CDCl$_3$): 0.88 (t, J=6.5 Hz, 3H); 1.12 to 1.40 (m, 20H); 1.81 (s, 3H); 170 to 185 (m, 1H); 1.85 to 2.00 (m, 1H); 5.62 (d, J=5.1 Hz, 0.5 H); 5.65 (d, J=5.0 Hz, 0.5 H); 6.17 (s, 1H); 7.33 to 7.50 (m, 5H).

$^{13}$C NMR (CDCl$_3$): 13.8, 20.1, 22.4, 25.3, 28.8, 29.1, 29.2, 29.3, 29.4, 31.7, 33.0, 70.3, 97.2, 128.6, 128.9, 129.4, 131.1, 156.8, 170.7, 171.3.

LRMS m/z calculated for $C_{25}H_{40}O_5$ (M+NH$_4$)—434, observed 434.

2-Methyl-4-phenyl-3-furaldehyde (Compound 58)

n-Butyllithium (a 1.6 m solution in hexane, 2.43 ml, 3.89 mmol) was added to a solution of trimethylethylenediamine (397 mg, 3.89 mmol) in tetrahydrofuran (25 ml) at 0 degrees under argon. After 20 minutes the solution was cooled to −78 degrees and 4-phenyl-3-furaldehyde (Compound 54, 608 mg, 3.35 mmol) was added. This mixture was allowed to gradually warm to −20 degrees and stirred for 1 ½ hours, then recooled to −78 degrees before n-butyllithium (a 1.6 M solution in hexane, 2.43 ml, 3.89 mmol) was added dropwise. The stirring mixture was again gradually warmed to −20 degrees and stirred for 2 hours before iodomethane (2.56 g 17.67 mmol) was added. After stirring for 18 hours at −20 degrees the reaction was quenched with ice-cold 10% (v/v) hydrochloric acid and the organics were extracted into ethyl ether. The combined fractions were washed with saturated sodium bicarbonate, H$_2$O and brine. Evaporation of the dried (magnesium sulfate) extracts gave an oil which was purified by flash chromatography on silica using 20% ethyl ether/hexanes to give the title aldehyde.

IR (CHCL$_3$): 3600, 1690 cm$^{-1}$.

$^1$H NMR (CDCl$_3$): 2.65 (s, 3H); 7.30 to 7.50 (m, 6H); 1.02 (s, 1H).

$^{13}$C NMR (CDCl$_3$): 13.4, 119.8, 127.2, 128.0, 128.7, 129.0, 130.6, 138.3, 162.3, 186.7.

HRMS: exact mass calculated for $C_{12}H_{10}O_2$ (M$^+$) 186.0680, found 186.0689.

2-Methyl-4-phenyl-3-furanmethanol (Compound 59)

LiAlH$_4$ (1.0 M solution in hexane, 0.12 ml,s 0.12 mmol) was added dropwise to a solution of 2-methyl-4-phenyl-3-furaldehyde (Compound 58, 45 mg, 0.24 mmol) in tetrahydrofuran (3 ml) at 0 degrees under argon. After 10 minutes the reaction was quenched with saturated ammonium chloride and the organics were extracted into ethyl ether. The combined fractions were washed with H$_2$O and brine and the dried (magnesium sulfate) extracts were concentrated to a yellow oil which was carried on without further purification.

IR (CHCl$_3$): 3620, 3450 (v. broad), 3005 cm$^{-1}$.

$^1$H NMR (CDCl$_3$): 2.38 (S, 3H); 4.56 (s, 2H); 7.25 to 7.60 (m, 6H).

$^{13}$C NMR (CDCl$_3$): 11.5, 54.8, 117.9, 127.2, 127.5, 128.1, 128.9, 132.7, 137.4, 151.9.

HRMS exact mass calculated for $C_{12}H_{12}O_2$ (M$^+$) 188.0837, found 188.0850.

3-Dodecoyloxymethyl-2-methyl-4-phenylfuran (Compound 60)

To a stirred solution of 2-methyl-4-phenyl-3-furanmethanol (Compound 59, 48 mg, 0.26 mmol) and triethylamine (39 mg. 0.38 mmol) in tetrahydrofuran (3 ml) at 0 degrees under argon was added lauroyl chloride (73 mg. 0.33 mmol). This solution was warmed gradually to room temperature and stirred for 4 ½ hours. The organics were extracted into ethyl ether and washed with a 5% aqueous sodium bicarbonate solution, H$_2$O and brine. Evaporation of the dried (magnesium sulfate) extracts gave an oil which was purified by flash chromatography on silica using 3% ether/hexanes to give the title compound.

IR (CHCl$_3$) 3010, 1725 cm$^{-1}$.

¹H NMR (CDCl₃): 0.86 (t, J=6.7 Hz, 3H); 1.20 to 1.32 (m, 16H); 1.50 to 1.64 (m, 2H); 2.23 to 2.32 (m, 2H); 2.36 (s, 3H); 4.97 (s, 2H); 7.29 to 7.42 (m, 6H)

¹³C NMR (CDCl₃): 11.7, 13.9, 22.5, 24.7, 28.9, 29.06, 29.12, 29.3, 29.4, 31.7, 34.2, 56.5, 113.7, 127.3, 127.9, 128.1, 128.8, 132.5, 137.6, 153.3, 174.1.

4-Dodecoyloxymethyl-5-hydroxy-5-methyl-3-phenyl-2-furanone (Compound 6)

A mixture of 3-dodecoyloxymethyl-2-methyl-4-phenylfuran (Compound 60, 40 mg, 0.11 mmol), water (a few drops) and Rose Bengal on polymer beads (240 mg) in tetrahydrofuran (40 ml) was exposed to singlet oxygen at 0 degrees for 3 hours. The Rose Bengal was filtered off and the residue was concentrated to a pink oil which was purified by flash chromatography on silica using 15% ethyl acetate/hexanes. The furanone was further purified by HPLC chromatography on a normal phase partisil 10 column using 15% ethyl acetate/hexanes to give the title compound.

IR (CHCl₃) 3020, 1765, 1740 cm⁻¹.

¹H NMR (CDCl₃): 0.85 (t, J=6.7 Hz, 3H); 1.10 to 1.21 (m, 16H); 1.35 to 1.49 (m, 2H); 1.77 (s, 3H); 2.11 (t, J=7.6 Hz, 2H); 3.70 to 3.90 (brs, 1H); 5.02 (s, 2H); 7.37 to 7.50 (m, 5H).

¹³C NMR (CDCl₃): 13.9, 22.5, 24.0, 24.4, 28.9, 29.0, 29.1, 29.2, 29.4, 31.7, 33.6, 57.2, 104.4 128.4, 128.7, 129.4, 129.8, 131.4, 154.4, 169.0, 173.9.

HRMS: exact mass calculated for $C_{24}H_{35}O_5(MH^-)$ 403.2484, found 403.2497.

5-Methyl-2-triethylsilyl-4-furanmethanol (Compound 61)

LiAlH₄ (1.0 M solution in hexane, 0.51 ml, 0.51 mmol) was added dropwise to a solution of 5-methyl-2-triethylsilyl-4-furaldehyde (Compound 38, 230 mg, 1.03 mmol) in tetrahydrofuran (15 ml) at 0 degrees under argon. The stirring solution was allowed to warm to room temperature gradually over ½ hour. The reaction was quenched with 10% aqueous HCl and the organics were extracted into ethyl ether. The combined fractions were washed with H₂O and brine. Evaporation of the dried (magnesium sulfate) extracts gave an oil which was purified by filtration through silica using 10% ethyl ether/hexanes to give the title compound.

IR (CHCl₃): 3610 (sharp), 3440 (broad), 2940 cm⁻¹.

¹H NMR (CDCl₃) 0.71 (q, J=7.7 Hz, 6H); 0.96 (t, J=7.7 Hz, 9H); 2.25 (s, 3H); 2.40 (brs, 1H); 4.38 (s, 2H); 6.59 (s, 1H).

¹³C NMR (CDCl₃): 2.9, 11.5, 56.2, 118.9, 122.3, 153.7, 156.0.

4-Dodecoyloxymethyl-5-methyl-2-triethylsilylfuran (Compound 62)

To a stirred solution of 5-methyl-2-triethylsilyl-4-furanmethanol (Compound 61, 208 mg, 0.92 mmol) and triethylamine (121 mg, 1.20 mmol) in tetrahydrofuran (10 ml) at 0 degrees under argon was added lauroyl chloride 302 mg, 1.38 mmol). This solution was allowed to warm gradually to room temperature and quenched with a 10% aqueous HCl solution. The organics were extracted into hexanes and the combined fractions were washed with a saturated aqueous solution of sodium bicarbonate, H₂O and brine. Evaporation of the dried (magnesium sulfate) extracts gave an oil which was purified by filtration through silica using 2% ethyl ether/hexanes to give compound.

IR (CHCl₃) 1725 cm⁻¹.

¹H NMR (CDCl₃) 0.75 (q, J=7.7 Hz, 6H); 0.88 (t, J=6.7 Hz, 3H), 0.98 (t, J=7.7 Hz, 9H); 1.20 to 1.35 (m, 16H); 1.56 to 1.68 (m, 2H); 2.30 (t, J=7.5 Hz, 2H); 2.31 (s, 3H); 4.91 (s, 2H); 6.57 (s, 1H).

¹³C NMR (CDCl₃): 2.9, 7.0, 11.7, 13.8, 22.6, 24.8, 28.9, 29.08, 29.14, 29.3, 29.4, 31.7, 34.2, 57.9, 114.7, 122.9, 155.3, 156.3, 174.2.

4-Dodecoyloxymethyl-5-hydroxy-5-methyl-2-furanone (Compound 7)

A mixture of 4-dodecoyloxymethyl-5-methyl-2-triethylsilylfuran (180 mg, 0.44 mmol), water (a few drops) and Rose Bengal on polymer beads (360 mg) in tetrahydrofuran (70 ml) was exposed to singlet oxygen at 0 degrees until no starting material was visible (via TLC). The Rose Bengal was filtered off and the residue was concentrated to a pink oil which was purified by flash chromatography on silica using 30% ethyl acetate/hexanes to give the titled furanone.

IR (CHCl₃): 3400 (v. broad), 1750 (strong) cm⁻¹.

¹H NMR (CDCl₃) 0.88 (t, J=6.7 Hz 3H); 1.20 to 1.37 (m, 16H); 1.59 to 1.70 (m, 2H); 1.72 (s, 3H); 2.40 (t, J=7.6 Hz, 2H); 3.20 to 4.40 (v. brs, 1H); 4.93 (s, 2H); 5.94 (s, 1H).

¹³C NMR (CDCl₃): 13.8, 22.4, 23.7, 24.5, 28.8, 28.9, 29.0, 29.2, 29.3, 31.6, 33.7, 58.4, 105.9, 117.0, 166.2, 170.3, 173.7.

3-Phenyl-2-triethylsilyl-4-furaldehyde (Compound 63)

n-Butyllithium (a 1.42 M solution in hexane, 2.33 ml, 3.31 mmol) was added to a solution of 1-methylpiperazine (331 mg, 3.31 mmol) in tetrahydrofuran (15 ml) at 0 degrees under argon. After 15 minutes the solution was cooled to −78 degrees and 4-phenyl-3-furaldehyde (Compound 54 517 mg, 3.01 mmol) was added. This mixture was warmed to 0 degrees and stirred for 15 minutes, then recooled to −78 degrees before sec-butyllithium (a 1.3 M solution in cyclohexane, 2.77 ml, 3.61 mmol) was added dropwise. This solution was stirred 12 hours at −78 degrees C. before chlorotriethylsilane (1.81 g, 12.02 mmol) was added. The mixture was allowed to warm gradually to room temperature and stirred an additional 1½ hours. The reaction was quenched with ice-cold 5% (V/V) hydrochloric acid and the organics were extracted into ethyl ether. The combined fractions were washed with saturated sodium bicarbonate, H₂O and brine. Evaporation of the dried (magnesium sulfate) extracts gave an oil which was purified by flash chromatography on silica using 10% ethyl acetate/hexanes to give the title aldehyde.

IR (heat): 2952, 1691 cm.

¹H NMR (CDCl₃) 0.62 (q, J=7.8 Hz, 6H); 0.85 (t, J=7.8 Hz, 9H); 7.20 to 7.43 (m, 5H); 8.30 (s, 1H); 9.79 (s, 1H).

¹³C NMR (CDCl₃): 3.0, 6.8, 127.1, 128.2, 130.2, 131.8, 136.5, 153.7, 158.3, 186.1.

3-Phenyl-2-triethylsilyl-4-furanmethanol (Compound 64)

LiAlH₄ (1.0 M solution in hexane, 1.48 ml, 1.48 mmol) was added dropwise to a solution of 3-phenyl-2-triethylsilyl-4-furaldehyde (Compound 63, 422 mg, 1.48 mmol) in tetrahydrofuran (10 ml) at 0 degrees under argon. This mixture was warmed to room temperature, quenched with ice-cold 5% (V/V) hydrochloric acid and the organics were extracted into ethyl ether. The combined fractions were washed with saturated sodium bicarbonate, H₂O and brine. The dried extracts (magnesium sulfate) were concentrated to an oil which was purified by flash chromatography on silica using 20% ethyl acetate/hexanes to give the title compound. IR (neat): 3300 (broad); 2953 cm⁻.

$^1$H NMR (CDCl$_3$): 0.59 (q, J=8.0 Hz, 6H); 0.85 (t, J=8.0 Hz, 9H); 1.60(brs, 1H); 4.42 (brs, 2H); 7.29 to 7.40 (m, 5H); 7.68 (s, 1H).

$^{13}$C NMR (CDCl$_3$): 3.2, 6.9, 55.2, 125.2, 127.6, 128.2, 130.0, 133.7, 137.5, 144.9, 155.7.

4-Dodecoyloxymethyl-3-phenyl-2-triethylsilylfuran (Compound 65)

To a stirred solution of 3-phenyl-2-triethylsilyl-4-furanmethanol (345 mg, 1.20 mmol) and triethylamine (182 mg, 1.80 mmol) in tetrahydrofuran (Compound 64, 15 ml) at 0 degrees under argon was added lauroyl chloride (786 mg, 3.60 mmol). This solution was allowed to warm gradually to room temperature. After stirring an additional 2 hours the white precipitate was filtered off. The filtrate was taken up into ethyl ether, washed with saturated ammonium chloride, saturated sodium bicarbonate, H$_2$O and brine. Evaporation of the dried (magnesium sulfate) extracts gave an oil which was purified by flash chromatography on silica using 2% ethyl ether/hexanes to give the title compound.

IR (neat): 1737 cm⁻¹.

$^1$H NMR (CDCl$_3$) 0.60 (q, J=8.1 Hz, 6H); 0.81 to 0.93 (m, 12H), 1.19 to 1.35 (m, 16H); 1.48 to 1.61 (m, 2H); (m, 2H); 2.23 (t, J=7.5 Hz, 2H); 4.86 (s, 2H); 7.25 to 7.40 (m, 5H); 7.72 (S, 1H).

—C NMR (CDCl$_3$) 3.17, 6.90, 13.8, 22.5, 24.7, 28.9, 29.0, 29.1, 29.2, 29.4, 31.7, 34.1, 56.4, 120.5, 127.6, 128.1, 130.1, 133.3, 138.0, 146.4, 155.6, 173.8.

4-Dodecoyloxymethyl-5-hydroxy-3-phenyl-2(5H)-furanone (Compound 66)

A mixture of 4-dodecoyloxymethyl-3-phenyl-2-triethylsiylfuran (Compound 65, 256 mg, 0.54 mmol), water (a few drops) and Rose Bengal on polymer beads (1.0 g) in tetrahydrofuran was exposed to singlet oxygen at 0 degrees for 3 hours. The Rose Bengal was filtered off and the residue was concentrated to a pink oil which was purified by flash chromatography on silica using 20% ethyl acetate/hexanes to give the title compound.

IR (CHCl$_3$): 3400 (v. broad), 1743 cm⁻¹.

$^1$H NMR (CDCl$_3$): 0.88 (t, J=6.6 Hz, 3H); 1.05 to 1.45 (m, 16H); 1.50 to 1.63 (m, 2H); 2.25 (t, J=7.6 Hz, 2H); 5.04 (S, 1H); 5.07 (S, 1H); 5.37 to 5.50 (brs, 1H); 6.22 (S, 1H); 7.40 to 7.54 (m, 5H).

$^{13}$C NMR (CDCl$_3$): 14.1, 22.6, 24.6, 29.0, 29.2, 29.3, 29.4, 29.5, 31.8, 33.8, 57.5, 96.5, 96.6, 128.1, 128.6, 129.1, 129.6, 131.7, 152.6, 170.5, 173.6.

What is claimed is:

1. A compound of the formula

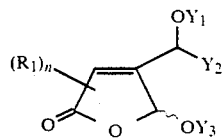

where:

R$_1$ independently is H, phenyl, C$_1$-C$_6$ alkyl substituted phenyl, halogen substituted phenyl, or alkyl of 1 to 6 carbons and n is an integer having the values of 1 or 2, and where when n is 1 the R$_1$ group is attached to one of the 3 and the 5 positions of the 2-furanone, when n is 2 then the R$_1$ groups are attached to both the 3 and 5 positions with the proviso that when n is 1 then R$_1$ is not H;

Y$_1$ is H, alkyl of 1 to 20 carbons, phenyl C$_1$-C$_{20}$ alkyl, C$_1$-C$_{20}$ alkenyl containing one or more olefinic bonds, PO(OH)$_2$, PO(OH)OR$_2$, PO(OH)R$_2$, PO-(OR$_2$)$_2$, where R$_2$ is independently alkyl of 1 to 20 carbons, phenyl, or halogen substituted phenyl or C$_1$-C$_6$ alkyl substituted phenyl, further Y$_1$ is CO—R$_3$, CO—OR$_3$, CONHR$_3$, SO$_2$R$_3$, (CH$_2$)$_p$—O—R$_3$, or (CH$_2$)$_p$—O—(CH$_2$)$_m$—O—R$_3$, where p, and m, are integers and are independently 1 to 20 and R$_3$ is H, C$_1$-C$_{20}$ alkyl, C$_1$-C$_{20}$ alkenyl containing one or more olefinic bonds, phenyl, halogen substituted phenyl or C$_1$-C$_6$ alkyl substituted phenyl, with the proviso that when Y$_1$ is CO—OR$_3$, or CONHR$_3$ then R$_3$ is not hydrogen;

Y$_2$ is H, an alkyl group of 6 to 25 carbons, phenyl, naphthyl, phenyl (C$_1$-C$_{20}$)alkyl—, naphthyl (C$_1$-C$_{20}$)alkyl—, C$_1$-C$_6$ alkyl substituted phenyl, halogen substituted naphthyl, C$_1$-C$_6$ substituted naphthyl, and Y$_3$ is H, alkyl of 1 to 20 carbons, CO—R$_4$, CO—O—R$_4$, CO—NH—R$_4$, PO(OR$_4$)$_2$or PO-(OR$_4$)R$_4$, where R$_4$ independently is H, alkyl of 1 to 20 carbons, phenyl, halogen substituted phenyl or C$_1$-C$_6$ alkyl substituted phenyl, with the proviso that when Y$_3$ is COOR$_4$ or CONHR$_4$ then R$_4$ is not H, or a pharmaceutically acceptable salt thereof.

2. A compound of claim 1 wherein Y$_1$ is H, CO—R$_3$, or CONHR$_3$.

3. A compound of claim 2 wherein R$_3$ is alkyl of 1 to 12 carbons or is phenyl.

4. A compound of the formula

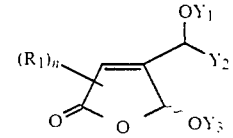

where:

R$_1$ independently is H, phenyl, C$_1$-C$_6$ alkyl substituted phenyl, halogen substituted phenyl, or alkyl or 1 to 6 carbons and n is an integer having the values of 1 or 2, and where when n is 1 the R$_1$ group is attached to one of the 3 and the 5 positions of the 2-furanone, when n is 2 then the R$_1$ groups are attached to both the 3 and 5 positions, with the proviso that when n is 1 then R$_1$ is not H;

Y$_1$ is CO—R$_3$ where R$_3$ is CH$_3$—or phenyl;

Y$_2$ is H, an alkyl group of 6 to 25 carbons, phenyl, naphthyl, phenyl (C$_1$-C$_{20}$)alkyl—, naphthyl (C$_1$-C$_{20}$)alkyl—, halogen substituted phenyl, C$_1$-C$_6$ alkyl substituted phenyl, halogen substituted naphthyl, C$_1$-C$_6$ substituted naphthyl, and Y$_3$ is H, alkyl of 1 to 20 carbons, CO—R$_4$, CO—O—R$_4$, CO—NH—R$_4$, PO(OR$_4$)$_2$ or PO-(OR$_4$)R$_4$, where R$_4$ independently is H, alkyl of 1 to 20 carbons, phenyl, halogen substituted phenyl or C$_1$-C$_6$ alkyl substituted phenyl, with the proviso that when Y$_3$ is COOR$_4$ or CONHR$_4$ then R$_4$ is not H, or a pharmaceutically acceptable salt thereof.

5. A compound of claim 1 where n is 1.

6. A compound of claim 5 where R$_1$ is methyl, ethyl, propyl, butyl or phenyl.

7. A compound of the formula

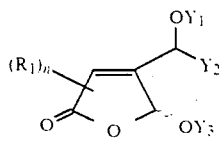

where:
- $R_1$ independently is H, phenyl, $C_1$-$C_6$ alkyl substituted phenyl, halogen substituted phenyl, or alkyl of 1 to 6 carbons, n is 2 and the $R_1$ groups are attached to both the 3 and 5 positions,
- $Y_1$ is H, alkyl of 1 to 20 carbons, phenyl $C_1$-$C_{20}$ alkyl, $C_1$-$C_{20}$ alkenyl containing one or more olephinic bonds, $PO(OH)_2$, $PO(OH)OR_2$, $PO(OH)R_2$, $PO(OR_2)_2$, where $R_2$ is independently alkyl of 1 to 20 carbons, phenyl, or halogen substituted phenyl or $C_1$-$C_6$ alkyl substituted phenyl, further $Y_1$ is $CO-R_3$, $CO-OR_3$, $CONHR_3$, $SO_2R_3$, $SO_2NHR_3$, $(CH_2)_p-O-R_3$, or $(CH_2)_p-O-(CH_2)_m-O-R_3$, where p, and m, are integers and are independently 1 to 20 and $R_3$ is H, $C_1$-$C_{20}$ alkyl, $C_1$-$C_{20}$ alkenyl containing one or more olefinic bonds, phenyl, halogen substituted phenyl or $C_1$-$C_6$ alkyl substituted phenyl, with the proviso that when $Y_1$ is $CO-OR_3$, and $CONHR_3$ then $R_3$ is not hydrogen;
- $Y_2$ is H, and
- $Y_3$ is H, alkyl of 1 to 20 carbons, $CO-R_4$, $CO-O-R_4$, $CO-NH-R_4$, $PO(OR_4)_2$ or $PO(OR_4)R_4$, where $R_4$ independently is H, alkyl of 1 to 20 carbons, phenyl, halogen substituted phenyl or $C_1$-$C_6$ alkyl substituted phenyl, with the proviso that when $Y_3$ is $COOR_4$ or $CONHR_4$ then $R_4$ is not H, or a pharmaceutically acceptable salt thereof.

8. A compound of claim 7 where $R_1$ is independently methyl, ethyl, propyl, butyl or phenyl.

9. A compound of claim 1 where $Y_3$ is H.

10. A compound of the formula

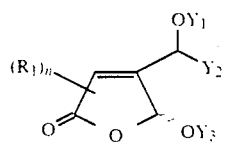

where:
- $R_1$ independently is H, phenyl, $C_1$-$c_6$ alkyl substituted phenyl, halogen substituted phenyl, or alkyl or 1 to 6 carbons and n is an integer having the values of 1 or 2, and where when n is 1 the $R_1$ group is attached to one of the 3 and the 5 positions of the 2-furanone, when n is 2 then the $R_1$ groups are attached to both the 3 and 5 positions, with the proviso that when n is 1 then $R_1$ is not H;
- $Y_1$ is H, alkyl of 1 to 20 carbons, phenyl $C_1$-$C_{20}$ alkyl, $C_1$-$C_{20}$ alkenyl containing one or more olephinic bonds, $PO(OH)_2$, $PO(OH)OR_2$, $PO(OH)R_2$, $PO(OR_2)_2$, where $R_2$ is independently alkyl of 1 to 20 carbons, phenyl, or halogen substituted phenyl or $C_1$-$C_6$ alkyl substituted phenyl, further $Y_1$ is $CO-R_3$, $CO-OR_3$, $CONHR_3$, $SO_2R_3$, $SO_2NHR_3$, $(CH_2)_p-O-R_3$, or $(CH_2)_p-O-(CH_2)_m-O-R_3$, where p, and m, are integers and are independently 1 to 20 and $R_3$ is H, $C_1$-$C_{20}$ alkyl, $C_1$-$C_{20}$ alkenyl containing one or more olefinic bonds, phenyl, halogen substituted phenyl or $C_1$-$C_6$ alkyl substituted phenyl, with the proviso that when $Y_1$ is $CO-OR_3$, and $CONHR_3$ then $R_3$ is not hydrogen;
- $Y_2$ is alkyl or 8 to 25 carbons, and
- $Y_3$ is H, alkyl of 1 to 20 carbons, $CO-R_4$, $CO-O-R_4$, $CO-NH-R_4$, $PO(OR_4)_2$ or $PO(OR_4)R_4$, where $R_4$ independently is H, alkyl of 1 to 20 carbons, phenyl, halogen substituted phenyl or $C_1$-$C_6$ alkyl substituted phenyl, with the proviso that when $Y_3$ is $COOR_4$ or $CONHR_4$ then $R_4$ is not H, or a pharmaceutically acceptable salt thereof.

11. A compound of the formula

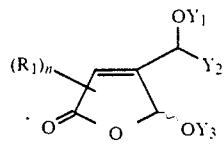

where
- $R_1$ independently is H, phenyl, or alkyl of 1 to 6 carbons and n is an integer having the values of 1 or 2, and where when n is 1 the $R_1$ group is attached to one of the 3 and the 5 positions of the 2-furanone, when n is 2 then the $R_1$ groups are attached to both the 3 and 5 positions with the proviso that when n is 1 then $R_1$ is not H;
- $Y_1$ is H, $CO$-$R_3$, $CONHR_3$, and $R_3$ is $C_1$-$C_{20}$ alkyl, $C_1$-$C_{20}$ alkenyl containing one or more olephinic bonds, phenyl, halogen substituted phenyl or $C_1$-$C_6$ alkyl substituted phenyl;
- $Y_2$ is H or an alkyl group of 1 to 25 carbons, with the further proviso that when n is 2 then $Y_2$ is H and
- $Y_3$ is H or $CO-R_4$, where $R_4$ is alkyl of 1 to 6 carbons, or a pharmaceutically acceptable salt thereof.

12. A compound of claim 11 where $Y_2$ is n-alkyl.

13. A compound of claim 11 where $Y_1$ is $CO-R_3$, $CONHR_3$, and $R_3$ is $CH_3CO$ or phenyl.

14. A compound of claim 11 where $Y_3$ is H.

15. A compound of claim 11 where n is 1 and the $R_1$ substituent is in the 5 position.

16. A compound of claim 11 where n is 1 and the $R_1$ substituent is in the 3 position.

17. A compound of claim 11 wherein n is 2 and the $R_1$ groups independently are methyl, butyl, or phenyl with the proviso that both $R_1$ groups are not phenyl.

18. A compound of claim 17 where Y is $CO-R_3$ and $R_3$ is $C_1$-$C_{20}$ alkyl.

19. A compound of the formula

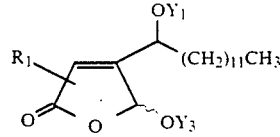

where:
- $R_1$ is phenyl, or alkyl of 1 to 6 carbons, the $R_1$ group being attached to one of the 3 and 5 positions of the 2-furanone;
- $Y_1$ is H, $COCH_3$, or $CONH-C_6H_5$;
- $Y_3$ is H, or $CO-R_4$, where $R_4$ independently is alkyl of 1 to 6 carbons, or a pharmaceutically acceptable salt thereof.

20. A compound of claim 19 where $Y_3$ is H.

21. A compound of claim 20 where $Y_1$ is $CH_3CO$, and $R_1$ is selected from methyl, butyl and phenyl.

22. A compound of claim 21 which is 4-(1-acetoxytridecyl)-5-hydroxy-5-methyl-2-furanone, 4-(1-acetoxytridecyl)-5-hydroxy-3-methyl-2(5H)-furanone, 4-(1-acetoxytridecyl)-5-hydroxy-5-phenyl-2-furanone, 4-(1-acetoxytridecyl)-5-hydroxy-3-phenyl-2(5H)-furanone, 4-(1-acetoxytridecyl)-5-hydroxy-5-butyl-2-furanone, or 4-(1-acetoxytridecyl)-5-hydroxy-3-butyl-2(5H)-furanone.

23. A compound of claim 20 where $Y_1$ is $CONH-C_6H_5$, and $R_1$ is selected from methyl, butyl and phenyl.

24. A compound of claim 23 which is 4-(1-phenylcarbamoyloxytridecyl)-5-hydroxy-5-methyl-2-furanone, 4-(1-phenylcarbamoyloxytridecyl)-5-hydroxy-3-methyl-2(5H)-furanone, 4-(1-phenylcarbamoyloxytridecyl)-5-hydroxy-5-phenyl-2-furanone, 4-(1-phenylcarbamoyloxytridecyl)-5-hydroxy-3-phenyl-2(5H) furanone, 4-(1 phenylcarbamoyloxytridecyl)-5-hydroxy-5-butyl-2-furanone, or 4-(1-phenylcarbamoyloxytridecyl)-5-hydroxy-3-butyl-2(5H)-furanone.

25. A compound of the formula

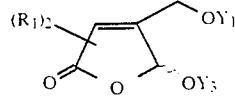

where $R_1$ independently is phenyl or alkyl of 1 to 6 carbons, the $R_1$ groups being attached to the 3 and 5 positions of the 2-furanone;
$Y_1$ is $CO-R_3$ or $CONHR_3$ and $R_3$ is $C_6-C_{20}$ alkyl, and
$Y_3$ is H or $CO-R_4$ where $R_4$ is alkyl of 1 to 6 carbons, or a pharmaceutically acceptable salt thereof.

26. A compound of claim 25 where $Y_3$ is H.

27. A compound of claim 25 where $Y_1$ is $CO-R_3$ and $R_3$ is $CH_3-(CH_2)_{10}$.

28. A compound of claim 27 which is 4-dodecoyloxymethyl-5-hydroxy-5-methyl-3-phenyl-2-furanone.

* * * * *

UNITED STATES PATENT AND TRADEMARK OFFICE
CERTIFICATE OF CORRECTION

PATENT NO. : 5,183,906

DATED : February 2, 1993

INVENTOR(S) : Gary C. M. Lee, et al.

It is certified that error appears in the above-identified patent and that said Letters Patent is hereby corrected as shown below:

Column 2, line 5, before "various" insert —having—;

Column 2, line 55, after "$SO_2NHR_3$," insert —$(CH_2)_p-O-R_3$, or—;

Column 3, line 61, ..."dohyde" should be ...—dehyde—;

Column 3, line 61, "Grigard" should be —Grignard—;

Column 4, lines 63-64, "diasteromeric" should be —diastereomeric", and after "optically" delete the —,—;

Column 8, line 5, "(Mobilization)" should be —(mobilization)—;

Column 11, line 52, after "which" insert —are—;

Column 12, line 42, after "23)" insert —.—;

Column 13, Reaction Scheme 4, Formula 18, the double bond O is missing.

Column 13, line 67, "phenyloyanide" should be —phenylcyanide";

Column 13, line 68, "5z" should be —52—;

Column 14, line 20, "3=substituted..." should be —3-substituted...—;

Column 16, line 13, after "hexane" change ":" to —;—;

Column 16, line 48, "-780°" should be — $-78°$ —;

Column 16, line 66, "8 25" should be —8.25—;

Column 17, line 24, after "abundance): delete the —.—; and after "183" insert —(M—before the "+";

Column 18, line 10, after "to" insert —a—;

Column 18, line 33, after "sulfate" insert —)—;

Column 18, line 61, "158 2" should be —158.2—;

Column 19, line 19, after "THF" change the ":" to —;—;

Column 19, line 56, "158" should be —168—;

UNITED STATES PATENT AND TRADEMARK OFFICE
CERTIFICATE OF CORRECTION

PATENT NO. : 5,183,906

DATED : February 2, 1993

INVENTOR(S) : Gary C. M. Lee, et al.

It is certified that error appears in the above-identified patent and that said Letters Patent is hereby corrected as shown below:

Column 20, line 28, insert a space before the "9.2" and "20 8" should be --20.8--;

Column 20, line 67, insert a space before the "0.24";

Column 21, line 5, "124 1" should be --124.1--;

Column 21, line 9, delete the "(" before the "2";

Column 23, line 1, "I53" should be --153--;

Column 23, line 28, "TUF" should be --THF--;

Column 23, line 65, "chenyl" should be --phenyl--;

Column 26, line 68, after "($CHCl_3$)" insert --:--;

Column 27, line 3, after "6H)" insert --.--;

Column 27, line 21, after "($CHCl_3$)" insert --:--;

Column 27, line 29, "(MH-)" should be --($MH^+$)--;

Column 27, line 47, after "($CDCl_3$)" insert --:--;

Column 27, line 67, after "give" insert --the title--;

Column 27, line 68, after "($CHCl_3$)" insert --:--;

Column 28, line 1, after "($CDCl_3$)" insert --:--;

Column 28, line 21, after "($CDCl_3$)" insert --:--;

Column 28, line 52, after "($CDCl_3$)" insert --:--;

Column 29, line 4, "$cm^-$." should be --$cm^{-1}$.--

Column 29, line 27, after "($CDCl_3$)" insert --:--;

Column 29, line 31, "-c" should be --$^{13}C$--;

Column 30, line 1, after "positions" insert --,--;

UNITED STATES PATENT AND TRADEMARK OFFICE
CERTIFICATE OF CORRECTION

PATENT NO. : 5,183,906

DATED : February 2, 1993

INVENTOR(S) : Gary C. M. Lee, et al.

It is certified that error appears in the above-identified patent and that said Letters Patent is hereby corrected as shown below:

Column 30, line 9, after "$SO_2R_3$," insert —$SO_2NHR_3$,—;

Column 30, line 28, "$Y_3$is" should be —$Y_3$ is—;

Column 30, line 46, "or" should be —of—;

Column 31, line 50, "or" should be —of—; (second occurrence);

Column 32, line 4, "or" should be —of—; and

Column 33, line 21, after ..."(5H)" insert — - —.

Signed and Sealed this

Twenty-fifth Day of January, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,183,906
DATED : February 2, 1993
INVENTOR(S) : Gary C. M. Lee, et al.

It is certified that error appears in the above-indentified patent and that said Letters Patent is hereby corrected as shown below:

Column 13, line 26, delete "a" (second occurrence);
Column 20, line 8, "1H)," should be —1H).—;
Column 20, line 11, "170.7," should be —170.7.—;
Column 28, line 51, "heat" should be —neat—; and
Column 28, line 51, "cm." should be —$cm^{-1}$.—.

Signed and Sealed this

Twenty-ninth Day of March, 1994

BRUCE LEHMAN

*Attest:*

*Attesting Officer*    Commissioner of Patents and Trademarks